US007829064B2

(12) United States Patent
Griffiths et al.

(10) Patent No.: US 7,829,064 B2
(45) Date of Patent: Nov. 9, 2010

(54) ANTI-CD74 IMMUNOCONJUGATES AND METHODS

(75) Inventors: Gary L. Griffiths, Morristown, NJ (US); Hans J. Hansen, Picayune, MS (US); David M. Goldenberg, Mendham, NJ (US); Bo B. Lundberg, Abo (FI)

(73) Assignee: Immunomedics, Inc., Morris Plains, NJ (US)

( * ) Notice: Subject to any disclaimer, the term of this patent is extended or adjusted under 35 U.S.C. 154(b) by 1169 days.

(21) Appl. No.: 10/706,852

(22) Filed: Nov. 12, 2003

(65) Prior Publication Data

US 2004/0219203 A1    Nov. 4, 2004

Related U.S. Application Data

(63) Continuation-in-part of application No. 10/314,330, filed on Dec. 9, 2002, which is a continuation of application No. 09/965,796, filed on Oct. 1, 2001, which is a continuation of application No. 09/307,816, filed on May 10, 1999, now Pat. No. 6,306,393, application No. 10/706,852, which is a continuation-in-part of application No. 10/350,096, filed on Jan. 24, 2003, which is a continuation of application No. 09/590,284, filed on Jun. 9, 2000, now Pat. No. 7,074,403, application No. 10/706,852, which is a continuation-in-part of application No. 10/377,122, filed on Mar. 3, 2003, now Pat. No. 7,312,318.

(60) Provisional application No. 60/478,830, filed on Jun. 17, 2003, provisional application No. 60/360,259, filed on Mar. 1, 2002.

(51) Int. Cl.
*A61K 9/127*    (2006.01)
*A61K 39/44*    (2006.01)
*A61K 51/12*    (2006.01)

(52) U.S. Cl. ............... 424/1.21; 424/178.1; 424/179.1; 424/180.1; 424/182.1; 424/450

(58) Field of Classification Search ................ None
See application file for complete search history.

(56) References Cited

U.S. PATENT DOCUMENTS

| | | | |
|---|---|---|---|
| 4,036,945 A | 7/1977 | Haber |
| 4,046,722 A | 9/1977 | Rowland |
| 4,331,647 A | 5/1982 | Goldenberg |
| 4,699,784 A | 10/1987 | Shih et al. |
| 4,704,692 A | 11/1987 | Ladner |
| 4,824,659 A | 4/1989 | Hawthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,620,708 A | 4/1997 | Amkraut et al. |
| 5,633,425 A | 5/1997 | Lonberg et al. |
| 5,686,072 A | 11/1997 | Uhr et al. |
| 5,702,727 A | 12/1997 | Amkraut et al. |
| 5,716,595 A | 2/1998 | Goldenberg |
| 5,736,119 A | 4/1998 | Goldenberg et al. |
| 5,776,456 A | 7/1998 | Anderson et al. |
| 5,789,554 A | 8/1998 | Leung et al. |
| 5,792,845 A * | 8/1998 | O'Reilly et al. ............ 536/23.1 |
| 5,795,967 A | 8/1998 | Aggarwal et al. |
| 5,798,554 A | 8/1998 | Grimaldi et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,077,499 A | 6/2000 | Griffiths et al. |
| 6,096,289 A | 8/2000 | Goldenberg |

(Continued)

FOREIGN PATENT DOCUMENTS

EP    0 332 865 A2    9/1989

(Continued)

OTHER PUBLICATIONS

Rudikoff et al (Proc Natl Acad Sci USA 1982 vol. 79 p. 1979).*

(Continued)

*Primary Examiner*—Karen A Canella
(74) *Attorney, Agent, or Firm*—Richard A. Nakashima

(57) ABSTRACT

Disclosed are compositions that include anti-CD74 immunoconjugates and a therapeutic and/or diagnostic agent. Also disclosed are methods for preparing the immunoconjugates and using the immunoconjugates in diagnostic and therapeutic procedures. The compositions may be part of a kit for administering the anti-CD74 immunoconjugates compositions in therapeutic and/or diagnostic methods.

109 Claims, 13 Drawing Sheets

U.S. PATENT DOCUMENTS

| | | | |
|---|---|---|---|
| 6,165,440 | A | 12/2000 | Esenaliev |
| 6,183,744 | B1 | 2/2001 | Goldenberg |
| 6,187,287 | B1 | 2/2001 | Leung et al. |
| 6,254,868 | B1 | 7/2001 | Leung et al. |
| 6,306,393 | B1 | 10/2001 | Goldenberg |
| 6,331,175 | B1 | 12/2001 | Goldenberg |
| 6,379,698 | B1 | 4/2002 | Leamon |
| 6,387,350 | B2 | 5/2002 | Goldenberg |
| 6,395,276 | B1* | 5/2002 | Rybak et al. ............. 424/179.1 |
| 6,530,944 | B2 | 3/2003 | West et al. |
| 6,562,318 | B1 | 5/2003 | Filler |
| 7,074,403 | B1* | 7/2006 | Goldenberg et al. ..... 424/130.1 |
| 7,387,779 | B2* | 6/2008 | Kalluri .................... 424/185.1 |
| 2002/0071807 | A1 | 6/2002 | Goldenberg |
| 2003/0082154 | A1 | 5/2003 | Leamon |
| 2003/0124058 | A1 | 7/2003 | Goldenberg |
| 2004/0076683 | A1* | 4/2004 | Hoarau et al. ............... 424/490 |

FOREIGN PATENT DOCUMENTS

| | | |
|---|---|---|
| EP | 0 510 949 A2 | 10/1992 |
| WO | WO 91/13974 | 9/1991 |
| WO | WO 94/27638 | 12/1994 |
| WO | WO 95/09917 | 4/1995 |
| WO | WO 96/04925 | 2/1996 |
| WO | WO 98/42378 | 10/1998 |
| WO | WO 98/50435 | 11/1998 |
| WO | WO 99/02567 | 1/1999 |
| WO | WO 99/54440 | 10/1999 |
| WO | WO 00/29584 A1 | 5/2000 |
| WO | WO 00/67795 | 11/2000 |
| WO | WO 00/74718 A1 | 12/2000 |

OTHER PUBLICATIONS

Breen et al, Clinical Immunology, 2003, vol. 109, pp. 119-129.*
Nagel et al, Leukemia, 2005, vol. 19, pp. 841-846.*
Schlom (In: Molecular Foundations of Oncology, Sameule Broader, Ed, 1991, pp. 95-134).*
Greenwood et al, 'Effector functions of atched sets of recombinant human IgG subclass antibodies', In: Protein engineering of antibody molecules, for therapetuic and Prophylatic Applications in Man, Clark, Ed., 1993, pp. 89 and 97).*
Nakagawa et al, (Journal of Neurooncology, 1999, vol. 45, pp. 175-183.*
Goto et al (Blood, 1994, vol. 84, pp. 1922-1930).*
Hannsen et al (Biochemical Journal, 1996, vol. 320, pp. 293-300).*
Kratz et al (Crit Rev Drug Carrier Sys, 1999, vol. 16, pp. 245-288).*
Torchilin et al (Crit Rev Ther Drug Carriers, 1991, vol. 7, pp. 275-308).*
Bagshawe et al (Curr Opin Immunol, 1999, vol. 11, pp. 579-583).*
Hua et al (Human Pathology, 1998, vol. 29, pp. 1441-1446).*
Hong et al (Journal of Pharmacy and Pharmacology, Jan. 2002, vol. 54, pp. 51-58).*
Ansel et al., *Pharmaceutical Dosage Forms and Drug Delivery Systems*, 5th Ed., Lea & Feibiger (1990).
Bally, et al., *J. Liposome Res.*, 8(3):299 (1998).
Bendas, *Biodrugs*, 15(4):215 (2001).
Bendig et al., *Methods: A Companion to Methods in Enzymology*, 8:83 (1995).
Bird et al., *TIBTECH*, 9:132 (1991).
Bom et al., *J. Controlled Release*, 74:325 (2001).
Carter et al., *Proc. Natl. Acad Sci. USA*, 89:4285 (1992).
Cochlovius et al., *Cancer Research*, 60: 4336 (2000).
Coligan et al (eds.), *Current Protocols in Immunology*, vol. 1, pp. 2.5.1-2.6.7; pp. 2.7.1-2.7.12; 2.8.1-2.8.10; 2.9.1-2.9.3, and 2.10-2.10.4, John Wiley & Sons (1991).
Coloma et al., *Nature Biotech*, 15:159 (1997).
Constantinides et al., *Pharm. Res.*, 17(2):175 (2000).
Courtenay-Luck, "Genetic Manipulation of Monoclonal Antibodies", *Monoclonal Antibodies: Production, Engineering, and Clinical Application*, pp. 166-179, Ritter et al., eds., Cambridge University Press (1995).
Edelman et al, *Methods in Enzymology*, vol. 1, p. 422, Academic Press (1955).
FitzGerald et al., *Protein Eng.*, 10(10):1221 (1997).
Flavell et al., *Cancer Res.*, 57:4824 (1997).
Freedman et al, "Non-Hodgkin's Lymphomas," in *Cancer Medicine*, vol. 2, 3rd Edition, pp. 2028-2068, Holland et al (eds.), Lea & Febiger (1993).
French et al., *Leukemia Res.*, 20(7):607 (Jul. 1996).
Gennaro, *Remington's Pharmaceutical Sciences*, 18th Ed., Mack Publishing Co. (1990).
Gennaro, *Remington's Pharmaceutical Sciences*, 19th Ed., vol. I and II, Mack Publishing Co. (1995).
Ghetie et al., *Cancer Res.*, 48:2610 (1988).
Goldenberg, *Scientific American, Science & Medicine*, 1:64 (1994).
Goldenberg, *Semin. Nucl. Med.*, 19(4):332 (1989).
Goldenberg, *CA-A Cancer J. for Clinicians*, 44(1):43 (1994).
*Goodman and Gilman's The Pharmacological Basis of Therapeutics*, 7th Ed., MacMillan Publishing Co. (1985).
Green et al, *Nature Genet.*, 7:13 (1994).
Hansen et al., *Biochem. J.*, 320:293 (1996).
Harlow & Lane (eds), *Antibodies, A Laboratory Manual*, Cold Spring Harbor Laboratory, NY (1988).
Hasan et al., *Prog. Clin. Biol. Res.*, 288:471 (1989).
Hekman et al., *Cancer Immunol. Immunother.*, 32:364 (1991).
Hess et al., *Blood*, 89(6): 2203 (1997).
Huse et al., *Science*, 246:1275 (1989).
Johnson et al., *Current Opin. Struct. Biol.*, 3:564 (1993).
Jones et al., *Nature*, 321:522 (1986).
Jori et al., *Photodynamic Therapy of Tumors and Other Diseases*, Libreria Progetto (1985).
Juweid et al, *Nuc. Med. Comm.*, 18:142 (1997).
Juweid et al., *Cancer Res.* (suppl.), 55:5899s (1995).
Kaminski et al., *New Eng. J. of Med.*, 329(7):459 (1993).
Kiesel et al., *Leukemia Res.*, 11(12):1119 (1987).
Kirpotin, et al, *Biochemistry*, 36:66 (1997).
Köhler et al., *Nature*, 256:495 (1975).
Koning et al., *Biochim. Biophys. Acta*, 1420:153 (1999).
Kreitman et al., *Cancer Research*, 53:819 (1993).
Larrick et al., *Methods: A Companion to Methods in Enzymology*, 2(2):106 (1991).
Leonard et al., *Blood*, 94(10), supp. 1, part 1, abstract #404 (1999).
Leung et al, *Hybridoma*, 13:469 (1994).
Leung et al., *J. Immunol.*, 154:5919 (1995).
Leung et al., *Mol. Immunol.*, 32(17/18):1413 (1995).
Levine et al., *Neurology*, 52(8):1701 (1999).
Li et al., *Cellular Immunol.*, 118:85 (1989).
Lonberg et al., *Nature*, 368:856 (1994).
Longo, *Curr. Opin. Oncol.*, 8:353 (1996).
Lopes de Menezes et al., *Cancer Res.*, 58:3320 (1998).
Lopes de Menezes, et al., *J. Liposome Res.*, 9(2):199 (1999).
Lundberg, *J. Pharm. Sci.*, 83(1):72 (1994).
Lundberg, *Int. J. Pharm.*, 109:73 (1994).
Lundberg et al., *Int. J. Pharm.*, 134:119 (1996).
Lundberg, *J. Pharm. Pharmacol.*, 49:16 (1997).
Lundberg, *Anti-Cancer Drug Design*, 13:453 (1998).
Lundberg et al., *J. Pharm. Pharmacol.*, 51:1099 (1999).
Lundberg et al, *Int. J. Pharm.*, 205:101 (2000).
Mack et al., *Proc. Natl. Acad. Sci. USA*, 92:7021 (1995).
Maloney et al., *Blood*, 84(8):2457 (1994).
Maranhão et al., *Cancer. Chemother. Pharmacol.*, 49:487 (2002).
McCafferty et al., *Nature*, 348:552 (1990).
Mendez et al., *Nature Genetics*, 15:146 (1997).
The Merck Manual of Diagnosis & Therapy, pp. 1474-1476, Chap. 180, 17th Ed., Beers et al., Merck Research Labs, Whitehouse Station, NJ (1999).
Mew el al., *J. Immunol.*, 130(3):1473 (1983).
Mew et al., *Cancer Res.*, 45:4380 (1985).
Moase et al., *Biochim. Biophys. Acta*, 1510:43 (2001).
Möller et al., *J. Biol. Regul. Homeost. Agents*, 14(4):299 (2000).

Mosmann, *J. Immunol. Meth.*, 65:55 (1983).
Nisonoff et al., *Arch. Biochem. Biophys.*, 89:230 (1960).
Ochakovskaya et al., *Clin. Cancer Res.*, 7(6):1505 (2001).
Orlandi et al., *Proc. Natl. Acad. Sci. USA*, 86:3833 (1989).
Oseroff et al., *Proc. Natl. Acad. Sci USA*, 83:8744 (1986).
Oseroff et al., *Photochem. Photobiol.*, 46:83 (1987).
Pastan et al., *Cell*, 47:641 (1986).
Patti et al., *Eur. J. Haematol.*, 51:18 (1993).
Pawlak-Byczkowska et al., *Cancer Res.*, 49:4568 (1989).
Pèlegrin et al., *Cancer*, 67:2529 (1991).
Perkins et al., Int. J. Pharm. 200:27 (2000).
Pirker et al., *J. Clin. Invest.*, 76:1261 (1985).
Porter, *Biochem. J.*, 73:119 (1959).
Press et al., *N. Eng. J. Med.*, 329(17):1219 (1993).
Press et al., *The Lancet*, 346:336 (1995).
Press, *Cancer Journal from Scientific American*, 4:S19 (1998).
Price, "Production and Characterization of Synthetic Peptide-Derived Antibodies", *Monoclonal Antibodies: Production, Engineering, and Clinical Application*, Ritter et al., eds., pp. 60-84, Cambridge University Press (1995).
Protheroe et al., *Rheumatology*, 38:1150 (1999).
Qu et al., *J. Immunol. Methods*, 213(2):131 (1998).
Qu et al., "Internalization and Cytotoxic Effects of a Humanized Anti-CD74 Antibody, LL1", *Proc. Ann. Meeting American Assoc. Cancer Res.*, New York, NY, vol. 43:255, XP001152818 (2002).
Raag et al., *FASEB*, 9:73 (1995).
Renner et al., *Leukemia*, 11, supp. 2:S55 (1997).
Riechmann et al., *Nature*, 332:323 (1988).
Rowan et al., *Immunology*, 95(3):427 (1998).
Ryser et al., *Proc. Natl. Acad. Sci. USA*, 75(8):3867 (1978).
Saltzman et al., *Biophys. J.*, 55:163 (1989).
Sandhu, *Crit. Rev. Biotech.*, 12(5/6):437 (1992).
Sherwood et al., *Bio/Technology*, 10:1446 (1992).
Shih et al., *Int. J. Cancer*, 41:832 (1988).
Shih et al., *Int. J. Cancer*, 46:1101 (1990).
Shih et al., *Int. J. Cancer*, 56:538 (1994).
Shih et al., *Cancer Immunol. Immunother.*, 49:208 (2000).

Singer et al., *J. Immun.*, 150:2844 (1993).
Stein et al., *Cancer Immunol. Immunother.*, 37(5):293 (1993).
Straubinger, et al., *Biochemistry*, 29:4929 (1990).
Tatsuta et al., *Lasers Surg. Med.*, 9:422 (1989).
Taylor et al., *Int. Immun.*, 6(4):579 (1994).
Tempest et al., *Biotechnology*, 9:266 (1991).
Theocharis et al., *Clin. Immunol. Immunopathol.*, 74(2):135 (1995).
Thorpe, *TIBTECH*, 11:42 (1993).
Torchilin, et al., *Proc. Natl. Acad. Sci. USA*, 100(10): 6039 (2003).
Upeslacis et al., "Modification of Antibodies by Chemical Methods", *Monoclonal Antibodies: Principles and Applications*, pp. 187-230, Birch et al. (eds.), Wiley-Liss (1995).
Van den Bergh, *Chem. Britain*, 22:430 (1986).
Vaughan et al., *Nat. Biotechnol.*, 14:309 (1996).
Verhoeyen et al., *Science*, 239:1534 (1988).
Vuist et al., *Cancer Res.*, 49:3783 (1989).
Ward et al., "Genetic Manipulation and Expression of Antibodies", *Monoclonal Antibodies: Principles and Applications*, pp. 137-185, Birch et al. (eds.), Wiley-Liss, Inc. (1995).
West et al., *Curr. Opin. Biotech.*, 11:215 (2000).
Wong, *Chemistry of Protein Conjugation and Cross-Linking*, CRC Press (1991).
Wrobel et al., *Biochimica et Biophysica Acta*, 1235:296 (1995).
Xu et al., *Mol. Cancer. Ther.*, 1:337 (2002).
Yu et al, *Int. J. Cancer*, 56:244 (1994).
Griffiths et al., "Cure of SCID Mice Bearing Human B-Lymphoma Xenografts by an Anti-CD74 Antibody-Anthracycline Drug Conjugate" (manuscript).
Lundberg et al., "Cellular Association and Cytotoxicity of Anti-CD74-Targeted Lipid Drug-Carriers in B Lymphoma Cells" (manuscript).
Zhengxing, Qu, et al., Poster, "Internalization and Cytoitoixic Effects of a Humanized Anti-CD74 Antibody, LL1," Annual Meeting of the American Association of Advancement of Cancer, Apr. 2002, San Francisco, CA
US 6,558,648, 05/2003, Griffiths et al. (withdrawn)

* cited by examiner

```
CAGATCCAGTTGGTGCAGTCTGGACCTGAGCTGAAGAAGCCTGGAGAGACAGTCAAGGTCACCTGCAAGACTTCTGGATATACCTTCACA
----------+---------+---------+---------+---------+---------+---------+---------+---------+    90
GTCTAGGTCAACCACGTCAGACCTGGACTCGACTTCTTCGGACCTCTCTGTCAGTTCCAGTGGACGTTCTGAAGACCTATATGGAAGTGT
 Q  I  Q  L  V  Q  S  G  P  E  L  K  K  P  G  E  T  V  K  V  T  C  K  T  S  G  Y  T  F  T
                       10                      20                      30

AACTATGGAGTGAACTGGATAAAGCAGACTCCAGGAGAGGGTTTACAGTGGATAAACCCAAACACTGGAGAGCCAACATTT
----------+---------+---------+---------+---------+---------+---------+---------+    180
TTGATACCTCACTTGACCTATTTCGTCTGAGGTCCTCTCCCAAATGTCACCTACCGACCTCTTTGGGTTGTGACCTCTCGGTTGTAAA
 N  Y  G  V  N  W  I  K  Q  T  P  G  E  G  L  Q  W  M  G  W  I  N  P  N  T  G  E  P  T  F
     CDR1                              40               50    52A          CDR2

GATGATGACTTCAAGGGACGATTTGCCTTCTCTCTTTGGAATCCTCCTGCCAGCACTGCCTTTTTGCAGATCAGCAACCTCAAAATGAGGAC
----------+---------+---------+---------+---------+---------+---------+---------+---------+    270
CTACTACTGAAGTTCCCTGCTAAACGGAAGAGAAACCTTAGGAGGACGGTCGTGACGGAAAACGTCTAGTCGTTGGAGTTTTTACTCCTG
 D  D  D  F  K  G  R  F  A  F  S  L  E  S  S  A  S  T  A  F  L  Q  I  S  N  L  K  N  E  D
 60                     70                      80          82A B  C

ATGGGTACATATTTCTGTTCAAGATCGAGGGGGTAAAAACGAAGCCTGGTTTGCTTATTGGGGCCAAGGGACTCTGGTCACTGTCTCTGAA
----------+---------+---------+---------+---------+---------+---------+---------+---------+    360
TACCCATGTATAAAGACAAGTTCTAGCTCCCCATTTTTGCTTCGGACCAAACGAATAACCCCGGTTCCCTGAGACCAGTGACAGAGACTT
 M  G  T  Y  F  C  S  R  S  R  G  K  N  E  A  W  F  A  Y  W  G  Q  G  T  L  V  T  V  S  E
                90          100A B  K               CDR3                 110
```

```
GATGTTGTGATGACCCAAACTCCACTCTCCCTGCCTGTCAGTCTTGGAGATCAAGCCTCCATCTCTTGCAGAGATCTAGTCAGAGCCTTGTA        90
CTACAACACTACTGGGTTTGAGGTGAGAGGGACGGACAGTCAGAACCTCTAGTTCGGAGTAGAAGACGTCTAGATCAGTCTCGGAACAT
 D  V  V  M  T  Q  T  P  L  S  L  P  V  S  L  G  D  Q  A  S  I  S  C  R  S  S  Q  S  L  V
                         10                      20                      27A B C
                                                                        CDR1

CACAGAAATGAAACACCTATTTACATTGGTACCTGCAGAAGCCAGGTCTCCAAAGCTCCTGATCTACACAGTTTCCAACCGATTT              180
GTGTCTTTACTTTGTGGATAAATGTAACCATGGACGTCTTCGGTCCAGAGGTTTCGAGGACTAGATGTGTCAAAGGTTGGCTAAA
 H  R  N  G  N  T  Y  L  H  W  Y  L  Q  K  P  G  Q  S  P  K  L  L  I  Y  T  V  S  N  R  F
            30                      40                      50
                                                                        CDR2

TCTGGGGTCCCAGACAGGTTCAGTGGCAGTGGATCAGGGACAGATTTCACACTCAAGATCAGTAGAGTGGAGGCTGAGGATCTGGGACTT        270
AGACCCCAGGGTCTGTCCAAGTCACCGTCACCTAGTCCCTGTCTAAAGTGTGAGTTCTAGTCATCTCACCTCCGACTCCTAGACCCTGAA
 S  G  V  P  D  R  F  S  G  S  G  S  G  T  D  F  T  L  K  I  S  R  V  E  A  E  D  L  G  L
            50                      60          70                      80

TATTTCTGCTCTCAAAGTTCACATGTTCCTCCCACGTTCGGTGGCTGACAAGCTGGAGATCTAAC                                337
ATAAAGACGAGAGTTTCAAGTGTACAAGGAGGGTGCAAGCCACCGACTGTTCGACCTCTAGATTG
 Y  F  C  S  Q  S  S  H  V  P  P  T  F  G  A  G  T  K  L  E  I
                  90                      100
                 CDR3
```

Figure 2A cLL1VH

```
CAGGTCCAACTGCAGCAGTCTGGACCTGAGCTGAAGAAGCCTGGAGAGACAGTCAAGATCACCTGCAAGACTTCTGGATATACTTTCACA      90
----+----+----+----+----+----+----+----+----+----+----+----+----+----+----+----+----+----+
GTCCAGGTTGACGTCGTCAGACCTGGACTCGACTTCTTCGGACCTCTCTGTCAGTTCTAGTGGACGTTCTGAAGACCTATATGAAGTGT
      [PstI]
 Q  V  Q  L  Q  Q  S  G  P  E  L  K  K  P  G  E  T  V  K  V  T  C  K  T  S  G  Y  T  F  T    30

AACTATGGAGTGAACTGGATAAAGCAGACTCCAGGAGAGGGTTTACAGTGGATGGGATAAACCCCAACACTGGAGAGCCAACATTT         180
----+----+----+----+----+----+----+----+----+----+----+----+----+----+----+----+----+----+
TTGATACCTCACTTGACCTATTTCGTCTGAGGTCCTCTCCCAAATGTCACCTACCCTATTTGGGGTTGTGACCTCTCGGTTGTAAA
  N  Y  G  V  N  W  I  K  Q  T  P  G  Q  G  L  Q  W  M  G  W  I  N  P  N  T  G  E  P  T  P    59
     CDR1                                                        CDR2

GATGATGACTTCAAGGACGATTTGCCTTCTTCTTTGCCAGATCCTCTGCAGCACTGGAGCACTGGACTCAACCTCAAAAATGAGGAC        270
----+----+----+----+----+----+----+----+----+----+----+----+----+----+----+----+----+----+
CTACTACTGAAGTTCCTGCTAAACGGAAGAAGAAACCTTAGGAGACGGTCGTGACCGTCTGTTGGAGTTTTTACTCCTG
 D  D  D  F  K  D  D  L  P  F  S  L  E  S  S  A  S  T  A  F  L  Q  I  S  N  L  K  N  E  D     89

ATGGGTTACATATTTTGTGTTCAAGATGAGGGTAAAACGAAGGCTCGTGTTTGCTTATTGGGCCAAGGGACTCTGGTCACGGTCTCCTCA    360
----+----+----+----+----+----+----+----+----+----+----+----+----+----+----+----+----+----+
TACCCATGTATAAAAGACAAGTTCTAGCTCCCATTTTGCTTCCGAGCACAAACGAATAACCCGGTTCCCTGAGACCAGTGCCAGAGGAGT
                                                                        [BstEII]
 M  G  T  Y  F  C  S  R  S  R  G  K  N  E  A  W  F  A  Y  W  G  Q  G  T  L  V  T  V  S  S    113
                             CDR3
```

Figure 2B cLL1Vk

```
                    PvuII
GACATCCTTGCAGACCCAAACTCCACTCTCCCTGCCTGTCAGTCTCTTGGAGATCAAGCCTCCATCTCTTGCAGATCTAGTCAGAGCCTTGTA
-------+---------+---------+---------+---------+---------+---------+---------+---------+      90
CTGTAGGAACGTCTGGGTTTGAGGTGAGAGGGACGGACAGTCAGAACCTCTAGTTCGGAGGTAGAGAAGCTCTAGATCAGTCTCGGAACAT

D  I  Q  L  T  Q  T  P  L  S  L  P  V  S  L  G  D  Q  A  S  =  S  C  R  S  S  Q  S  L  V    270
                                                                     CDR1

CACAGAAATGGAAACACCTATTTACATTGGTACCTGCAGAAGCCAGGCCAGTCTCCAAAGCTCCTGATCTACACAGAGTTTCAAACCGATTT
-------+---------+---------+---------+---------+---------+---------+---------+---------+     180
GTGTCTTTACCTTTGTGGATAAATGTAACCATGGACGTCTTCGGTCCGGTCAGAGGTTTCGAGGACTAGATGTGTCTCAAAGTTGGCTAAA

H  R  N  G  N  T  Y  L  H  W  Y  L  Q  K  P  G  Q  S  P  K  L  L  I  Y  T  V  S  N  R  F    55
       CDR1                                                          CDR2

TCTGGGGTCCCAGACAGGTTCAGTGGCAGTGGATCAGGGACAGATTTCACACTCAAGATCAGTAGAGTGGAGGCTGAGGATCTGGGACTT
-------+---------+---------+---------+---------+---------+---------+---------+---------+     270
AGACCCCAGGGTCTGTCCAAGTCACCGTCACCTAGTCCCTGTCTAAAGTGTGAGTTCTAGTCATCTCACCTCCGACTCCTAGACCCTGAA

S  G  V  P  D  R  F  S  G  S  G  S  G  T  D  F  T  L  K  I  S  R  V  E  A  E  D  L  G  L    85
                                                                                        BglII/BclI
TATTTCTGCTCTCAAAGTTCACATGTTCCTCCACGTTCGGTGTCACCAAGCTGGAGATCAAACGT
-------+---------+---------+---------+---------+---------+---      339
ATAAAGACGAGAGTTTCAAGTGTACAAGGAGGTGCAAGCCACAGACCCTGGTTCGACCTCTAGTTTGCA

Y  F  C  S  Q  S  S  H  V  P  P  T  F  G  A  G  T  K  L  E  I  K  R                         108
            CDR3
```

Figure 3A

```
RF-TS3   QVQLVQSGSELKKPGASVKVSCKASGYTFTSYAMNWVRQA  40
cLL1VH   QVQLQ••••P••••ET••T•••••••••N•GV••IK•T    40
hLL1VH   QVQLQ•••••••••••••••••••••••N•GV••IK••    40

RF-TS3   PGQGLEWMGWINTNTGNPTYAQGFTGRFVFSLDTSVSTAY  79
cLL1VH   ••E••Q••••P••E••FDDD•••A•••ES•A•••F       79
hLL1VH   ••Q••••••••••E••FDDD•••A•••••••••         79

RF-TS3   LQISSLKADDTAVYYCAREDSNGYKIFDY            102
cLL1VH   ••••N••NE••MGT•F•S•SRGKNEAW•A            113
hLL1VH   •••••••••••••••F•S•SRGKNEAW•A            113

NEWM     WGQGSLVTVSS                              113
cLL1VH   ••••••T••TVSS                            113
hLL1VH   •••••••TVSS                              113
```

Figure 3B

```
HF-21/28  DVVMTQSPLSLPVTLGQPASISCRSSQSLVHSDGNTYLNW  35
cLL1Vk    DIQL..T.....S.DQ...................RN....H  35
hLL1Vk    DIQL.....................................RN....H  35

HF-21/28  YLFQQRPGQSPRRLIYKVSNRDSGVPDRFSGSGSGTDFTLKI  75
cLL1Vk    YL.....L...KL...T...F....................  75
hLL1Vk    .......L.....T...F.......................  75

HF-21/28  SRVEAEDVGVYYCMQGTHWPFTFGQGTRLEI  106
cLL1Vk    ........L...F..S.SS.V.P...A.K..IKR  108
hLL1Vk    ...........F..S.SS.V.P...A....IKR  108
```

Figure 4A hLL1VH

```
CAGGTCCAACTGCAGCAATCTGGGGCTGAGTTGAAGAAGCCTGGGGCCTCAGTGAAGGTTTCCTGCAAGGCTTCTGGATACACCTTCACT      90
----------+---------+---------+---------+---------+---------+---------+---------+---------+
GTCCAGGTTGACGTCGTTAGACCCCGACTCAACTTCTTCGGACCCCGGAGTCACTTCCAAAGGACGTTCCGAAGACCTATGTGGAAGTGA

Q  V  Q  L  Q  Q  S  G  S  E  L  K  K  P  G  A  S  V  K  V  S  C  K  A  S  G  Y  T  F  T     30

AACTATGGAGTGAACTGGATAAAGCAGGCCCCTGGACAAGGCCTTGAGTGGATGGGCTGGATAAACCCCAACACTGGAGAGCCAACATTT     180
----------+---------+---------+---------+---------+---------+---------+---------+---------+
TTGATACCTCACTTGACCTATTTCGTCCGGGGACCTGTTCCGGAAGTCACCTACCCGACCTATTTGGGGTTGTGACCTCTCGGTTGTAAA

N  Y  G  V  N  W  I  K  Q  A  P  G  Q  G  L  E  W  M  G  W  I  N  P  N  T  G  E  P  T  F     59
  CDR1                                                      CDR2

GATGATGACTTCAAGGGACGATTTGCCTTCTCTCTGGACACCTCTGTCAGCACGGCATATCTCCAGATCAGCAGCCTAAAGGCTGACGAC     270
----------+---------+---------+---------+---------+---------+---------+---------+---------+
CTACTACTGAAGTTCCCTGCTAAACGGAAGAGAGACCTGTGGAGACAGTCGTGCCGTATAGAGGTCTAGTCGTCGGATTTCCGACTGCTG

D  D  D  F  K  G  R  F  A  F  S  L  D  T  S  V  S  T  A  Y  L  Q  I  S  S  L  K  A  D  D     89

ACTGCCGTGTATTTCTGTTCAAGATCGAGGGGTAAAAACGAAGCCTGGTTTGCTTATTGGGGCCAAGGGACCCTGGTCACCGTCTCCTCA     360
----------+---------+---------+---------+---------+---------+---------+---------+---------+
TGACGGCACATAAAGACAAGTTCTAGCTCCCCATTTTTGCTTCGGACCAAACGAATAACCCCGGTTCCCTGGGACCAGTGGCAGAGGAGT

T  A  V  Y  F  C  S  R  S  R  G  K  N  E  A  W  F  A  Y  W  G  Q  G  T  L  V  T  V  S  S     113
                      CDR3
```

Figure 4B hLL1Vk

```
GACATCCAGCTGACTCAGTCTCCACTCTCCCTGCCCGTCACCCTTGGACAGCCGGCCTCCA:CTCCTGCAGATCAAGTCAGAGCCTTGTA
----------+---------+---------+---------+---------+---------+---------+---------+---------+   90
CTGTAGGTCGACTGAGTCAGAGGTGAGAGGGACGGGCAGTGGGAACCTGTCGGCCGGAGGTGAGGACGTCTAGTTCAGTCTCGGAACAT

D  I  Q  L  T  Q  S  P  L  S  P  V  T  L  G  Q  P  A  S  :  S  C  R  S  S  Q  S  L  V
                                                                      CDR1

CACAGAAATGGAAACACCTATTTACATTGGTTTCAGCAGAGGCCAATCTCCAAGGCTCCTGATCTACACAGTTTCCAACCGATTT
----------+---------+---------+---------+---------+---------+---------+---------+---------+  180
GTGTCTTTACCTTTGTGGATAAATGTAACCAAAGTCGTCTCCGGTTAGAGGTTCCGAGGACTAGATGTGTCAAAGGTTGGCTAAA

H  R  N  G  N  T  Y  L  H  W  F  Q  Q  R  P  G  Q  S  P  R  L  L  I  Y  T  V  S  N  R  F
      CDR1                                                                     CDR2

TCTGGGGTCCCAGACAGATTCAGCGGCAGTGGGTCAGGGACTGATTTCACACTGAAAATCAGCAGGGTGGAGGCTGAGGATGTGGGGTT
----------+---------+---------+---------+---------+---------+---------+---------+---------+  270
AGACCCCAGGGTCTGTCTAAGTCGCCGTCACCCAGTCCCTGACTAAAGTGTGACTTTTAGTCGTCCCACCTCCGACTCCTACAACCCAA

S  G  V  P  D  R  F  S  G  S  G  S  G  T  D  F  T  L  K  I  S  R  V  E  A  E  D  V  G  V

TATTTCTGCTCTCAAAGTTCACATGTTCCTCCACGTTCGGTGCTGGGACAACGACTGGAGATCAAACGT
----------+---------+---------+---------+---------+---------+--------   339
ATAAAGACGAGAGTTTCAAGTGTACAAGGAGGTGCAAGCCACGACCCTGTGCTGACCTCTAGTTTGCA

Y  F  C  S  Q  S  S  H  V  P  P  T  F  G  A  G  T  R  L  E  I  K  R
              CDR3
```

ANTI-CD74 IMMUNOCONJUGATES AND METHODS

CROSS-REFERENCE TO RELATED APPLICATIONS

This application is a continuation-in-part of application Ser. No. 10/314,330, filed on Dec. 9, 2002, which is a continuation of application Ser. No. 09/965,796, filed on Oct. 1, 2001, which is a continuation of application Ser. No. 09/307,816, filed on May 10, 1999, now U.S. Pat. No. 6,306,393. This application is a continuation-in-part of application Ser. No. 10/350,096, filed on Jan. 24, 2003, which is a continuation of application Ser. No. 09/590,284, filed on Jun. 9, 2000. This application is a continuation-in-part of application Ser. No. 10/377,122, filed on Mar. 3, 2003, which claims the benefit of provisional application Ser. No. 60/360,259, filed on Mar. 1, 2002. This application claims the benefit of provisional application Ser. No. 60/478,830, filed on Jun. 17, 2003. All of the above-identified applications and patents are incorporated herein by reference in their entireties.

BACKGROUND

Conventional therapeutic agents do not distinguish between normal cells and diseased cells, and therefore conventional agents can damage and kill normal proliferating cells and tissues. To reduce the toxic side effects of conventional agents, the agents can be specifically targeted to the diseased cells or tissues. One method of specifically targeting therapeutic agents to diseased cells or tissues relies on the use of specific binding molecules such as antibodies or fragments thereof, and in particular, monoclonal antibodies.

The use of targeting binding molecues (e.g., monoclonal antibodies) conjugated to therapeutic or diagnostic agents offers the possibility of delivering such agents directly to the targeted cells or tissue (e.g., a tumor), thereby limiting the exposure of normal tissues to toxic agents (Goldenberg, *Semin. Nucl. Med.*, 19: 332 (1989)). In recent years, the potential of antibody-based therapy and its accuracy in the localization of antigens, such as tumor-associated antigens, have been demonstrated both in the laboratory and clinical studies (see, e.g., Thorpe, *TIBTECH*, 11: 42 (1993); Goldenberg, *Scientific American, Science & Medicine*, 1: 64 (1994); Baldwin et al., U.S. Pat. No. 4,925,922 and 4,916,2,13; Young, U.S. Pat. No. 4,918,163; U.S. Pat. No. 5,204,095; Irie et al., U.S. Pat. No. 5,196,337; Hellstrom et al., U.S. Pat. Nos. 5,134,075 and 5,171,665). For tumors, the use of radio-labeled antibodies or antibody fragments against tumor-associated markers for localization has been more successful than for therapy, in part because antibody uptake by the tumor is generally low, ranging from only 0.01% to 0.001% of the total dose injected (Vaughan et al., *Brit. J. Radiol.*, 60: 567 (1987)). Increasing the concentration of the radiolabel to increase the dosage to the tumor is counterproductive, generally, as this also increases exposure of healthy tissue to radioactivity. As such, a method of increasing uptake of therapeutic or diagnostic agents is desirable.

While therapeutic or diagnostic agents may be directed conjugated to an antibody as a targeting agent, the agents also may be indirectly associated with an antibody. For example, liposomes, nanoparticles, and polymers have been used as carriers for therapeutic agents, where antibodies may be conjugated to the carrier to provide specific targeting of the carrier/agent complex to a diseased cell or tissue. (See, e.g., Xu et al., *Mol. Cancer. Ther.*, 1:337-346 (2002); Torchilin, et al., *Proc. Nat'l. Acad. Sci.*, 10: 6039 (2003); U.S. Pat. Nos. 6,165,440; 5,702,727; 5,620,708; 5,565,215; 6,530,944; 6,562,318; 6,558,648; and 6,395,276). However, to facilitate uptake of the complex into the cell, it is important to select antibody/antigen partners where the antigen is rapidly cycled from the surface of the targeted cell to the interior of the targeted cell. One such antigen is CD74, which is an epitope of the major histocompatibility complex (MHC) class II antigen invariant chain, Ii, present on the cell surface and taken up in large amounts of up to $8\times10^6$ molecules per cell per day (Hansen et al., *Biochem. J.*, 320: 293-300 (1996). CD74 is present on the cell surface of B-lymphocytes, monocytes and histocytes, human B-lymphoma cell lines, melanomas, T-cell lymphomas and a variety of other tumor cell types. (Id.)

Murine LL1 (mLL1 or murine anti-CD74 antibody) is a specific monoclonal antibody (mAb) reactive with CD74. Cell surface-bound LL1 is rapidly internalized to the lysosomal compartment and quickly catabolized, much faster than other mAbs, such as anti-CD19 and anti-CD22. (Id.) This inherent property of LL1 overcomes some of the aforementioned difficulties with immunotherapy.

Murine LL1 was developed by fusion of mouse myeloma cells with splenocytes from BALB/c mice immunized with preparations from the Raji B-lymphoma cell line (called EPB-1 in Pawlak-Byczkowska et al., *Can. Res.*, 49: 4568 (1989)). The clinical use of mLL1, just as with most other promising murine antibodies, has been limited by the development in humans of a human anti-mouse antibody (HAMA) response. A HAMA response is generally not observed following injection of mLL1 Fab', as evidenced in a bone marrow imaging study using re a mLL1 Fab' labeled with $^{99m}$Tc. Juweid et al., *Nuc. Med. Comm.* 18: 142-148 (1997). However, in some therapeutic and diagnostic uses, a full-length anti-CD74 mAb may be preferred. This use of the full-length anti-CD74 mAb can limit the diagnostic and therapeutic usefulness of such antibodies and antibody conjugates, not only because of the potential anaphylactic problem, but also as a major portion of the circulating conjugate may be complexed to and sequestered by the circulating anti-mouse antibodies. Although the use of antibody fragments of mLL1 may circumvent the problems of immunogenicity, there are circumstances in which whole IgG is more desirable and the induction of cellular immunity is intended for therapy or enhanced antibody survival time. In general, HAMA responses pose a potential obstacle to realizing the full diagnostic and therapeutic potential of murine anti-CD74 mAbs. Therefore, the development of immunoconjugates that include chimeric, humanized and human anti-CD74 binding molecules, (e.g., mAbs and fragments thereof, antibody fusion proteins thereof and fragments thereof, multivalent and/or multispecific mAbs and fragments thereof), would be extremely useful for therapy and diagnosis, with reduced production of human anti-mouse antibodies.

SUMMARY

Disclosed is a composition that includes an effector molecule (e.g., a therapeutic or diagnostic agent) and an immunoconjugate, where the immunoconjugate includes an anti-CD74 binding molecule conjugated to one or more carriers. The carrier is capable of delivering the effector and may include molecules that can form a higher-ordered structure, (such as lipids or polymers), or the carrier may be a higher-ordered structure itself, (such as a micelle, liposome, or nanoparticle). The effector molecule may be covalently or non-covalently associated with the anti-CD74 binding molecule, the carrier, or both. In one embodiment, the composition comprises an emulsion or a liposome.

The anti-CD74 binding molecule may be conjugated or linked to the carrier by a number of linkages including sulfide linkages, hydrazone linkages, hydrazine linkages, ester linkages, amido linkages, amino linkages, imino linkages, thiosemicarbazone linkages, semicarbazone linkages, oxime linkages, and carbon-carbon linkages. A sulfide linkage may be preferred, where the binding molecule may include disulfide linkages, which may be reduced to provide free thiol groups.

The composition may include additional binding molecules, (e.g., antibodies or fragments thereof that bind to CD19, CD20, CD22, CD30, CD33, CD52, CD80, HLA-DR, MUC1, TAC, IL-6, tensascin, VEGF, placental growth factor, carbonic anhydrase IX, and mixtures thereof). The additional binding molecules may be covalently or non-covalently associated with any component of the composition (e.g., the carrier).

Where the carrier is a lipid, preferably the lipid is capable of forming an emulsion or a higher-ordered structure such as a micelle or liposome. For example, the lipid may be amphiphilic. To facilitate conjugation to the anti-CD74 binding molecule, the lipid may contain one or more groups capable of reacting with the anti-CD74 binding molecule, such as nucleophilic carbons, (e.g., at a distal terminus). In one embodiment, the lipid is polyethyleneglycol (PEG)-maleimide and the anti-CD74 binding molecule reacts via free thiol groups with the maleimide group. Maleimide groups may also be present on other carriers as described herein for conjugating the anti-CD74 binding molecule. For example, nanoparticles may contain maleimide groups for conjugating the anti-CD74 binding molecule. In addition to maleimide groups, other groups for conjugating binding molecules may include vinylsulfones.

In addition to the effector, which may include one or more therapeutic or diagnostic agents, the composition may further include additional therapeutic or diagnostic agents, which may be covalently, non-covalently, or otherwise associated with any component of the composition. For example, the additional therapeutic or diagnostic agent may be covalently linked to the anti-CD74 binding molecule. Alternatively, the additional therapeutic or diagnostic agent may be covalently linked to the carrier or non-covalently or otherwise associated with the carrier.

The effector may include any number of therapeutic or diagnostic agents. For example, the effector may include a drug, prodrug, toxin, enzyme, radioisotope, immunomodulator, cytokine, hormone, binding molecule (e.g., an antibody), or an oligonucleotide molecule (e.g., an antisense molecule or a gene). Antisense molecules may include antisense molecules that correspond to bcl-2 or p53. The effector may include aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5 '-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, *Staphylococcal* enterotoxin-A, pokeweed antiviral protein, gelonin, diphtheria toxin, *Pseudomonas* exotoxin, and *Pseudomonas* endotoxin, or combinations thereof. In certain embodiments, the effector includes FUdR, or FUdR-dO.

The composition may also include one or more hard acid chelators or soft acid chelators. For example, the chelator may include NOTA, DOTA, DTPA, TETA, Tscg-Cys, or Tsca-Cys. In certain embodiments, the chelators may form complexes with cations selected from Group II, Group III, Group IV, Group V, transition, lanthanide or actinide metal cations, or mixtures thereof. Alternatively, the cations may be covalently, non-covalently, or otherwise associated with any component of the complex. In certain embodiments, the composition includes cations selected from Tc, Re, Bi, Cu, As, Ag, Au, At, or Pb.

The composition may also include a nuclide (e.g., a radionuclide). The nuclide may be selected from a number of nuclides including $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Ga, $^{67}$Ga, $^{68}$Ga, $^{75}$Se, $^{77}$As, $^{86}$Y $^{89}$Sr, $^{89}$Zr, $^{90}$Y, $^{94}$Tc, $^{94m}$Tc, $^{99}$Mo, $^{99m}$Tc, $^{105}$Pd, $^{105}$Rh, $^{111}$Ag, $^{111}$In, $^{123}$I, $^{124}$I, $^{125}$I, 131I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb $^{212}$Bi, $^{212}$Pb, $^{213}$Bi, $^{223}$Ra, or $^{225}$Ac.

Where the effector is an enzyme, suitable enzymes may include carboxylesterases, glucoronidases, carboxypeptidases, beta-lactamases, phosphatases, and mixtures thereof. Where the effector is an immunomodulator, suitable immunomodulators may include IL-1, IL-2, IL-3, IL-6, IL-10, IL-12, IL-18, IL-21, interferon-α, interferon-β, interferon-γ, G-CSF, GM-CSF, and mixtures thereof. The effector may also include an anti-angiogenic agent, e.g., angiostatin, endostatin, basculostatin, canstatin, maspin, anti-VEGF binding molecules, anti-placental growth factor binding molecules, or anti-vascular growth factor binding molecules.

Preferably, the anti-CD74 binding molecule may be LL1 or a fragment thereof, although any anti-CD74 binding molecule is suitable. For example, production of monoclonal antibodies is well known in the art. See Harlow & Lane (eds), *Antibodies. A Laboratory Manual*, Cold Spring Harbor Laboratory, NY. However, human, chimeric, or humanized derivatives of LL1 or fragments thereof may be particularly suitable. Derivatives of LL1 are described in U.S. application Ser. No. 10/377,122, and U.S. application Ser. No. 60/360,259, filed Mar. 1, 2002, which are incorporated herein by reference in their entireties. The anti-CD74 binding molecule or fragment thereof may be monoclonal.

The anti-CD74 binding molecule may include a human, chimeric, or humanized anti-CD74 antibody or fragment thereof. For example, a binding molecule may contain CDRs of a light chain variable region of a murine anti-CD74 mAb. A humanized anti-CD74 antibody or fragment may include a heavy chain variable region of a humanized mAb, which may include CDRs of a heavy chain variable region of a murine anti-CD74 mAb. A humanized anti-CD74 antibody or fragment thereof may include light and heavy chain variable regions including complementarity-determining regions (CDRs) of murine anti-CD74 (mLL1) and a framework (FR) regions of a human antibody, where a light chain variable region of a humanized anti-CD74 mAb includes CDRs of a light chain variable region of a murine anti-CD74 mAb, and where a heavy chain variable region of a humanized mAb includes CDRs of a heavy chain variable region of a murine anti-CD74 mAb. A humanized anti-CD74 antibody or fragment thereof may include FRs of light and heavy chain variable regions of a humanized anti-CD74 antibody or fragment thereof, which may be substituted with at least one amino acid from corresponding FRs of a murine mAb. A mAb or fragment may include a humanized IgG 1.

A anti-CD74 binding molecule may be a chimeric anti-CD74 antibody or fragment thereof and may include a light chain variable region of a murine anti-CD74 mAb. For example, A chimeric anti-CD74 antibody or fragment thereof may include a heavy chain variable region of a murine anti-CD74 mAb. A chimeric anti-CD74 antibody or fragment thereof also may include light and heavy chain variable regions which may include complementarity-determining regions (CDRs) of a murine anti-CD74 mAb; framework (FR) regions of a murine anti-CD 74 mAb; and light and heavy chain constant regions of a human antibody, where light chain variable region of the chimeric mAb may include CDRs of a light chain variable region of a murine anti-CD74 mAb. A chimeric mAb or fragment thereof may include a chimeric IgG1 or fragment thereof.

Where the anti-CD74 binding molecule includes a human anti-CD74 antibody or fragment thereof, the binding molecule may include a light chain variable region of a human anti-CD74 mAb. For example, a human anti-CD74 antibody or fragment thereof may include a heavy chain variable region of the human mAb which may include CDRs of a heavy chain variable region of a murine anti-CD74 mAb. In another example, a human anti-CD74 antibody or fragment thereof may include the light and heavy chain variable and constant regions of a human antibody. A human mAb or fragment thereof may include a human IgG1.

The anti-CD74 binding molecule may be selected such that the binding of the molecule or fragment thereof to CD-74 is blocked by an antibody of fragment thereof specific for CD74. Alternatively, the binding molecule may be selected such that the mAb or fragment thereof is internalized by Raji lymphoma cells in culture. In another embodiment, an anti-CD74 binding molecule, such as a mAb or fragment thereof, may be selected such that it induces apoptosis of Raji cells in cell culture when cross-linked with goat antisera reactive with the Fc of a murine IgG1 mAb.

The anti-CD74 binding molecule may also include a fragment which includes a F(ab')$_2$, Fab, scFv, Fv, or a fusion protein utilizing part or all of the light and heavy chains of the F(ab')$_2$, Fab, scFv, or Fv, such that the fragment is capable of binding to CD74. The binding molecule may be selected or designed to be multivalent, or multivalent and multispecific. The fragments may form a bispecific binding molecule or a diabody. In one embodiment, the binding molecule,includes a fusion protein that includes four or more Fvs, or Fab's of the mAbs or fragments thereof. In a further embodiment, the binding molecule includes a fusion protein that includes one or more Fvs, or Fab's of an anti-CD74 mAb or fragment thereof, and one or more Fvs or Fab's from an antibody specific for a tumor cell marker that is not a CD74 antigen. For example, the tumor cell marker may include a B-cell lineage antigen such as CD19, CD20, or CD22. Alternatively, the tumor cell marker may include HLA-DR, CD30, CD33, CD52, MUC1, or TAC.

The anti-CD 74 binding molecule may include constant regions of IgG1, which are replaced with human constant regions of human IgG2a, IgG3, or IgG4.

Also disclosed is a method for treating and/or diagnosing a disease or disorder that includes administering to a patient a therapeutic and/or diagnostic composition. The therapeutic and/or diagnostic composition includes any of the aforementioned compositions, generally a composition that includes: (1) an effector molecule (e.g., a therapeutic or diagnostic agent); (2) an anti-CD74 binding molecule or fragment thereof conjugated to one or more carriers; and (3) a pharmaceutically acceptable excipient. Typically, the composition is administered to the patient intravenously or intramuscularly at a dose of 20-5000 mg.

The disease or disorder is typically a CD74-expressing malignancy, which may include an immune dysregulation disease, an autoimmune disease, an organ-graft rejection, a graft-versus-host disease, a solid tumor, non-Hodgkin's lymphoma, Hodgkin's lymphoma, multiple myeloma, a B-cell malignancy, or a T-cell malignancy. A B-cell malignancy may-include indolent forms of B-cell lymphomas, aggressive forms of B-cell lymphomas, chronic lymphatic leukemias, acute lymphatic leukemias, and/or multiple myeloma. Solid tumors may include melanomas, carcinomas, sarcomas, and/or gliomas. A carcinoma may include renal carcinoma, lung carcinoma, intestinal carcinoma, stomach carcinoma, breast carcinoma, prostate cancer, ovarian cancer, and/or melanoma.

In one embodiment, the composition may comprise an agent for photodynamic therapy, e.g., a photosensitizer such as a benzoporphyrin monoacid ring A (BDP-MA), tin etiopurpurin (SnET2), sulfonated aluminum phthalocyanine (AISPc), or lutetium texaphyrin (Lutex). The method may also include administering an irradiating light source to the targeted cells or tissue. In certain embodiments, photodynamic therapy may be used diagnostically as well as therapeutically.

The method may include administering a composition that includes a diagnostic nuclide, e.g., $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, $^{111}$In, $^{123}$I, $^{124}$I, $^{125}$I. $^{131}$I. Typically, the diagnostic nuclide will emit 25-4000 keV gamma particles and/or positrons.

The method may include administering a composition that includes a diagnostic agent, which can be used to perform positron emission tomography (PET). As such, the method may include performing positron-emission tomography (PET).

The method may include administering a composition that includes one or more image enhancing agents, e.g., gadolinium ions, lanthanum ions, manganese ions, iron, chromium, copper, cobalt, nickel, fluorine, dysprosium, rhenium, europium, terbium, holmium, neodymium, or mixtures thereof. As such, the method may include performing an imaging technique such as magnetic resonance imaging (MRI).

The method may include administering a composition that includes one or more radioopaque agents or contrast agents such as barium, diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof. The method may include performing an X-ray or computed tomography (CT).

The method may include administering a composition that includes one or more ultrasound contrast agents, such as dextran or a liposome (e.g., a gas-filled liposome). The method may include performing an ultrasound procedure.

In addition to the aforementioned procedures, the method may also include performing an operative, intravascular, laparoscopic, or endoscopic procedure, before, simultaneously, or after the immunoconjugate or composition is administered.

The method may also include administering a second or additional composition that includes a therapeutic or diagnostic agent, where the second or additional composition is administered before, simultaneously, or after the first composition is administered. The second or additional composition may include any of the aforementioned compositions. In one embodiment the second or additional composition includes an anti-CD74 binding molecule conjugated to a therapeutic or diagnostic agent. The therapeutic or diagnostic agent may comprise any of the aforementioned drugs, prodrugs, toxins, enzymes, radioisotopes, immunomodulators, cytokines, hormones, antibodies, binding molecules, oligonucleotides, chelators, cations, therapeutic nuclides, agents for photodynamic therapy, diagnostic nuclides, image enhancing agents, radioopaque agents, and/or contrasting agents. The method may also include performing a PET, MRI, X-ray, CT, ultrasound, operative, intravascular, laparoscopic, or endoscopic procedure.

Also disclosed are methods of preparing the aforementioned compositions (e.g., an anti-CD74 immunoconjugate by mixing one or more amphiphilic lipids with an effector to form a lipid drug-carrier and contacting the lipid drug-carrier with an anti-CD74 binding molecule, (e.g., an antibody or fragment thereof)). In one example, the lipid contains nucleophilic carbons (e.g., within a maleimide group), and the binding molecule contains free thiol groups (e.g., disulfides treated with a reducing agent). The method may include mixing the composition with one or more therapeutic or diagnostic agents, which may be covalently, non-covalently, or otherwise associated with any component of the composition.

Also disclosed is a kit that includes any of the aforementioned compositions or the components sufficient for preparing any of the aforementioned compositions. Typically, the kit includes instructions for administering the compositions or, where applicable, instructions for preparing the compositions.

BRIEF DESCRIPTION OF THE DRAWINGS

FIG. 1. DNA and amino acid sequences of the murine LL1 heavy and light chain variable regions. FIG. 1A shows DNA (SEQ ID NO: 1) and amino acid sequences (SEQ ID NO: 2) of LL1VH. FIG. 1B shows DNA (SEQ ID NO: 3) and amino acid sequences (SEQ ID NO: 4) of the LL1Vk. Amino acid sequences encoded by the corresponding DNA sequences are given as one-letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The residues numbered by a letter following a particular digit indicates the insertion residues defined by Kabat numbering scheme. The insertion residues numbered with a letter have the same preceding digit. For example, residues 82A, 82B and 82C in FIG. 1A are indicated as 82A, B, and C.

FIG. 2. DNA and amino acid sequences of chimeric LL1 (cLL1) heavy and light chain variable region. (See, U.S. Ser. No. 10/377,122.) FIG. 2A shows DNA (SEQ ID NO: 5) and amino acid sequences (SEQ ID NO: 6) of cLL1VH. FIG. 2B shows double-stranded DNA (SEQ ID NO: 7) and amino acid sequences (SEQ ID NO: 8) of cLL1Vk. Amino acid sequences encoded by the corresponding DNA sequences are given as one-letter codes. The amino acid residues in the CDR regions are shown in bold and underlined. The numbering of nucleotides and amino acids is same as that in FIG. 1.

FIG. 3. Alignment of amino acid sequences of light and heavy chain variable regions of a human antibody, cLL1 and hLL1. FIG. 3A shows the VH amino acid sequence alignment of the human antibody RF-TS3 (SEQ ID NO: 13), cLL1 (SEQ ID NO: 6), hLL1 (SEQ ID NO: 10), and NEWM (SEQ ID NO: 14) and FIG. 3B shows the Vk amino acid sequence alignment of the human antibody HF-21/28 (SEQ ID NO: 15), cLL1 (SEQ ID NO: 8) and hLL1 (SEQ ID NO: 12). Dots indicate the residues in cLL1 that are identical to the corresponding residues in the human antibodies. Boxed regions represent the CDR regions. Both N- and C-terminal residues (underlined) of cLL1 are fixed by the staging vectors used and not compared with the human antibodies. Kabat's Ig molecule number scheme is used as in FIG. 1.

FIG. 4. DNA and amino acid sequences of humanized LL1 (hLL1) heavy and light chain variable regions. FIG. 4A shows the DNA (SEQ ID NO: 9) and amino acid sequences (SEQ ID NO: 10) of hLL1VH and FIG. 4B shows the DNA (SEQ ID NO: 11) and amino acid sequences (SEQ ID NO: 12) of hLL1Vk. Amino acid sequences encoded by the corresponding DNA sequences are given as one letter codes. The amino acid residues in the CDR regions are shown in bold and underlined. Kabat's Ig molecule numbering scheme is used for amino acid residues as in FIG. 1A and FIG. 1B.

DETAILED DESCRIPTION

Definitions

Figure 5:
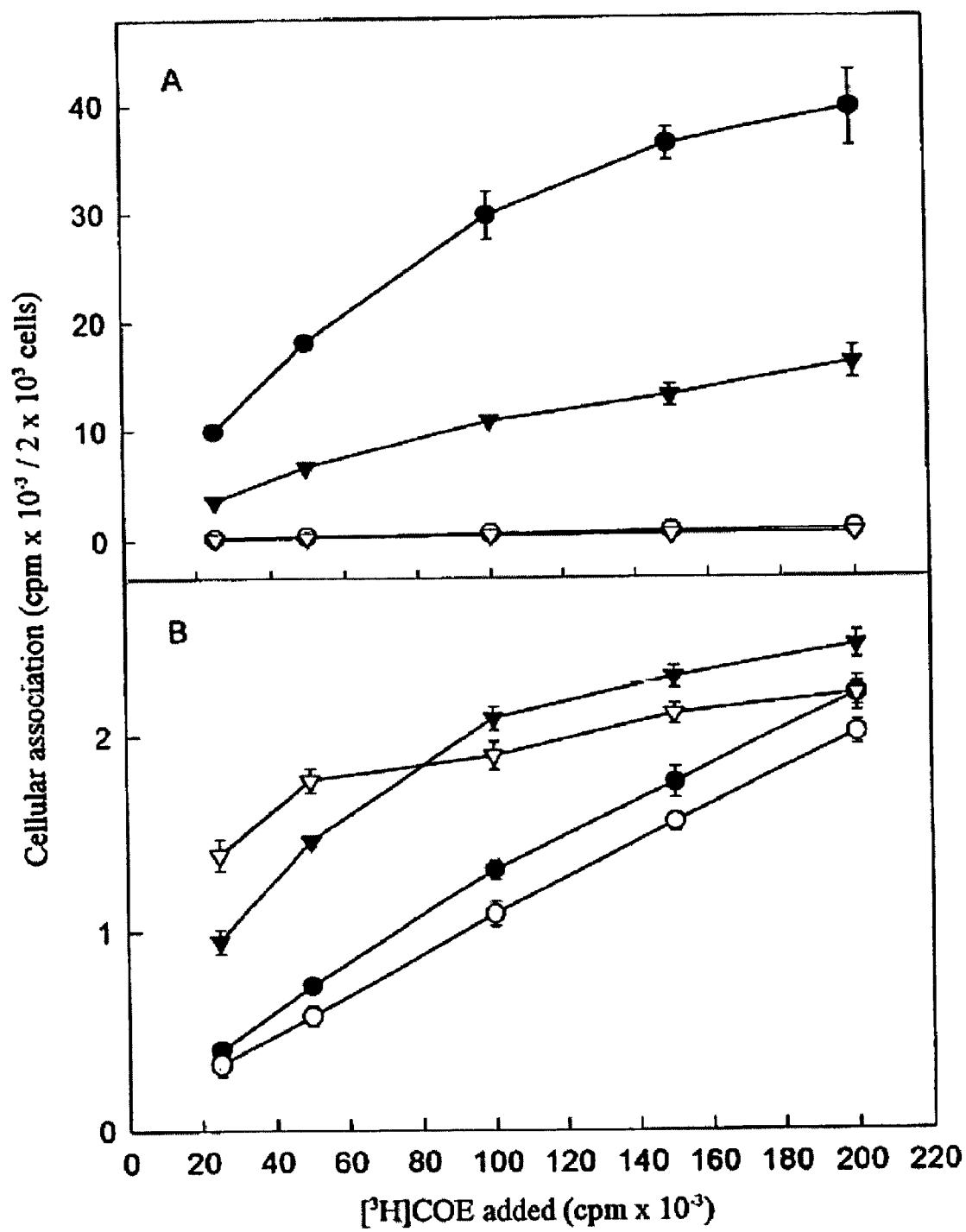
FIG. 5. Concentration-dependent cellular association of [$^3$H] Cholesteryl oleoyl ether (COE)-labeled, targeted and untargeted, drug-carrier emulsions during a 24-h incubation at 37° C. A. Top panel. Raji cells were treated with LL1-conjugated emulsions (●) and unconjugated emulsions (○). Ramos cells were treated with LL1-conjugated emulsions (▼) and unconjugated emulsions (▽). B. Bottom panel. HL-60 cells were treated with LL1-conjugated emulsions (●) and unconjugated emulsions (○). Jurkat cells were treated with LL1-conjugated emulsions (▼) and unconjugated emulsions (▽). (Mean±SE, n=4).

In the description that follows, a number of terms are used and the following definitions are provided to facilitate understanding of the disclosure herein.

A binding molecule, as described herein, is any molecule that can specifically bind to an antigen. A binding molecule may include an antibody or a fragment thereof. An anti-CD74 binding molecule is a molecule that specifically binds to the CD74 antigen, such as an anti-CD74 antibody or fragment thereof. Other anti-CD74 binding molecules may also include multivalent molecules, multispecific molecules (e.g., diabodies), fusion molecules, or other naturally occurring or recombinately created molecules.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab)$_2$, F(ab)$_2$, Fab, Fab, Fv, sFv and the like. Regardless of structure, an antibody fragment binds with the same antigen that is recognized by the intact antibody. For example, an anti-CD74 monoclonal antibody fragment binds with an epitope of CD74. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. (See, e.g., McCafferty et al., *Nature* 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, *Current Opinion in Structural Biology* 3:5564-571 (1993). Human antibodies may also be generated by in vitro activated B cells. (See, U.S. Pat. Nos. 5,567,610 and 5,229,275, which are incorporated in their entirety by reference).

An effector is an atom, molecule, or compound that brings about a chosen result. An effector may include a therapeutic agent and/or a diagnostic agent as described herein.

A therapeutic agent is an atom, molecule, or compound that is useful in the treatment of a disease. Examples of therapeutic agents include antibodies, antibody fragments, drugs, toxins, enzymes, nucleases, hormones, immunomodulators, antisense oligonucleotides, chelators, boron compounds, photoactive agents or dyes and radioisotopes.

A diagnostic agent is an atom, molecule, or comound that is useful in diagnosing a disease. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis- thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include, such as $^{18}$F, $^{52}$Fe, $^{62}$Cu, $^{64}$Cu, $^{67}$Cu, $^{67}$Ga, $^{68}$Ga, $^{86}$y, $^{89}$Zr, $^{94}$Tc, $^{94}$Tc, $^{94m}$Tc, $^{99m}$Tc, or $^{111}$In. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT may be used.

An immunoconjugate is a conjugate of a binding molecule (e.g., an antibody component) with an atom, molecule, or a higher-ordered structure (e.g., with a carrier, a therapeutic agent, or a diagnostic agent). The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A naked antibody is an antibody that is not conjugated to any other agent.

A carrier is an atom, molecule, or higher-ordered structure that is capable of associating with a therapeutic or diagnostic agent to facilitate delivery of the agent to a targeted cell. Carriers may include molecules such as lipids or polymers (e.g., amphiphilic lipids that are capable of forming higher-ordered structures, or carbohydrates such as dextran), or higher-ordered structures themselves, such as micelles, liposomes, or nanoparticles.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

A nanoparticle refers to a particle of size ranging from 1 to 1000 nm. Typically, a nanoparticle is biodegradable, biocompatible, and it functions as a carrier capable of incorporating the substance to be delivered to a targeted cell.

Preparation of Monoclonal Antibodies including Chimeric, Humanized and Human Antibodies The immunoconjugates and compositions described herein my include monoclonal antibodies. Rodent monoclonal antibodies to specific antigens may be obtained by methods known to those skilled in the art. (See, e.g., Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991)).

General techniques for cloning murine immunoglobulin variable domains have been described, for example, by the publication of Orlandi et al., *Proc. Nat'l Acad. Sci. USA* 86: 3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the V and $V_H$ domains of LL2 monoclonal antibody, an anti-CD22 antibody, with respective human and $IgG_1$ constant region domains. This publication also provides the nucleotide sequences of the LL2 light and heavy chain variable regions, V and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Humanized antibodies and antibody fragments are described in Provisional U.S. Application titled "Anti-CD20 Antibodies And Fusion Proteins Thereof And Methods Of Use", U.S. Provisional No. 60/356,132 filed Feb. 14, 2002; U.S. Provisional Application No. 60/416,232 filed Oct. 7, 2002; and U.S. Provisional Application No. 60/366,709 filed Feb. 14, 2003. Other humanized antibodies include hMN-14 antibodies, such as those disclosed in U.S. application Ser.

No. 5,874,540, which recognize a Class III anti-carcinoembryonic antigen antibody (anti-CEA antibody); Mu-9 antibodies, such as those described in U.S. application Ser. No. 10/116,116; AFP antibodies, such as those described in U.S. Provisional Application No. 60/399,707 filed Aug. 1, 2002; PAM4 antibodies, such as those described in Provisional U.S. Application 60/388/313, filed Jun. 14, 2002; RS7 antibodies, such as those described in U.S. Provisional Application No. 60/360,229, filed Mar. 1, 2002; and CD22 antibodies, such as those disclosed in U.S. Pat. Nos. 5,789,554 and 6,187,287 and U.S. application Ser. Nos. 09/741,843, 09/988,013, and U.S. Ser. No. 10/377,122 all of which are incorporated herein by reference in their entirety.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric mAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., *Biotechnology* 9:266 (1991) and Verhoeyen et al., *Science* 239: 1534 (1988)). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. (See, e.g., WO0029584A1).

A fully human antibody, i.e., human anti-CD74 MAbs or other human antibodies, such as anti-CD22, anti-CD19, anti-CD23, anti-CD20 or anti-CD21 MAbs for combination therapy with humanized, chimeric or human anti-CD74 antibodies, can be obtained from a transgenic non-human animal. (See, e.g., Mendez et al., *Nature Genetics*, 15: 146-156 (1997)); U.S. Pat. No. 5,633,425, which are incorporated in their entirety by reference. For example, a human antibody can be recovered from a transgenic mouse possessing human immunoglobulin loci.

Further recent methods for producing bispecific mAbs include engineered recombinant mAbs which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., *Nature Biotech*. 15:159-163, (1997)). A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Production of Antibody Fragments

Antibody fragments which recognize specific epitopes can be generated by known techniques. The antibody fragments are antigen binding portions of an antibody, such as $F(ab')_2$, Fab', Fab, Fv, sFv and the like. Other antibody fragments include, but are not limited to: the $F(ab)'_2$ fragments which can be produced by pepsin digestion of the antibody molecule and the Fab' fragments, which can be generated by reducing disulfide bridges of the $F(ab)'_2$ fragments. Alternatively, Fab' expression expression libraries can be constructed (Huse et al., 1989, *Science*, 246:1274-1281) to allow rapid and easy identification of monoclonal Fab' fragments with the desired specificity. The present targeted drug carriers may encompass both antibodies and antibody fragments.

A single chain Fv molecule (scFv) comprises a VL domain and a VH domain. The VL and VH domains associate to form a target binding site. These two domains are further covalently linked by a peptide linker (L). An scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. Nos. 4,704,692, 4,946,778, R. Raag and M. Whitlow, "*Single Chain Fvs*." FASEB Vol 9:73-80 (1995) and R. E. Bird and B. W. Walker, "*Single Chain Antibody Variable Regions*," TIBTECH, Vol 9: 132-137 (1991). These references are incorporated herein by reference.

An antibody fragment can be prepared by known methods, for example, as disclosed by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL.1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Anti-CD74 Antibodies

The anti-CD74 binding molecules of the present immunoconjugates and compositions may contain specific murine CDRs that have specificity for the CD74 antigen. For example, the anti-CD74 binding molecules may be humanized, chimeric or human mAbs, and they may contain the amino acids of the CDRs of a murine anti-CD74 mAb, (e.g., the murine anti-CD74 mAb, LL1). Humanized, chimeric, and human anti-CD74 mAb or fragments thereof are described in U.S. Ser. No. 10/377,122, which is incorporated herein by reference.

Where the anti-CD74 antibody is humanized, it may contain CDRs of a light chain variable region of a murine anti-CD74 mAb (e.g., a CDR1 including an amino acid sequence RSSQSLVHRNGNTYLH (SEQ ID N0:16); a CDR2 including an amino acid sequence TVSNRFS (SEQ ID NO: 17); and a CDR3 including an amino acid sequence SQSSHVPPT (SEQ ID NO: 18)). The humanized anti-CD74 antibody or fragment may include the heavy chain variable region of the humanized mAb, which may include CDRs of a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). The humanized anti-CD74 antibody or fragment thereof may include light and heavy chain variable regions including complementarity-determining regions (CDRs) of murine anti-CD74 (mLL1) and the framework (FR) regions of a human antibody, where the light chain variable region of the humanized anti-CD74 mAb includes CDRs of a light chain variable region of a murine anti-CD74 mAb (e.g., a CDR1 including an amino acid sequence RSSQSLVHRNGNTYLH (SEQ ID NO: 16); a CDR2 including an amino acid sequence TVSNRFS (SEQ ID NO: 17); and a CDR3 including an amino acid sequence SQSSHVPPT (SEQ ID NO: 18)), and where the heavy chain variable region of the humanized mAb includes CDRs of a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). The humanized anti-CD74 antibody or fragment thereof may include the FRs of the light and heavy chain variable regions of the humanized anti-CD74 antibody or fragment thereof, which may be substituted with at least one amino acid from the corresponding FRs of the murine mAb. In one embodiment, the substituted amino acid may be selected from amino acid residue 2, 3, 4, 46, 87 and 100 of the murine light chain variable region of the cLL1Vk sequence of FIG. 3B, and amino acid residues 5, 37, 38, 46, 68, 91 and 93 of the murine heavy chain variable region of the cLL1VH sequence of FIG. 3A. In another embodiment, the mAb or fragment thereof comprises a heavy chain variable region of FIG. 4A and a light chain variable region of FIG. 4B. In a further embodiment, the mAb or fragment thereof may comprise a light and heavy chain constant region of a human antibody or a portion thereof. The mAb or fragment may include a humanized IgG1.

Where the anti-CD74 binding molecule includes a chimeric anti-CD74 antibody, the chimeric anti-CD74 antibody or fragment thereof may include a light chain variable region of a murine anti-CD74 mAb (e.g., a CDR1 including an amino acid sequence RSSQSLVHRNGNTYLH (SEQ ID NO:16); a CDR2 including an amino acid sequence TVSNRFS (SEQ ID NO: 17); and a CDR3 including an amino acid sequence SQSSHVPPT (SEQ ID NO: 18)). In another embodiment, the chimeric anti-CD74 antibody or fragment thereof may include a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). In a further embodiment, The chimeric anti-CD74 antibody or fragment thereof may include light and heavy chain variable regions which may include complementarity-determining regions (CDRs) of a murine anti-CD74 mAb; the framework (FR) regions of a murine anti-CD 74 mAb; and the light and heavy chain constant regions of a human antibody, where the light chain variable region of the chimeric mAb may include CDRs of a light chain variable region of a murine anti-CD74 mAb (e.g., a CDR1 including an amino acid sequence RSSQSLVHRNGNTYLH (SEQ ID NO: 16); a CDR2 including an amino acid sequence TVSNRFS (SEQ ID NO: 17); and a CDR3 including an amino acid sequence SQSSHVPPT (SEQ ID NO: 18)); and where the heavy chain variable region of the chimeric mAb may include CDRs of a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). Alternatively, the chimeric mAb or fragment thereof may include a heavy chain variable region of FIG. 2A and a light chain variable region of FIG. 2B. The chimeric mAb or fragment thereof may include a chimeric IgG1 or fragment thereof.

Where the anti-CD74 binding molecule is a human anti-CD74 antibody, the human anti-CD74 antibody or fragment thereof may include a light chain variable region of the human anti-CD74 mAb (e.g., a CDR1 including an amino acid sequence RSSQSLVHRNGNTYLH (SEQ ID NO:16); a CDR2 including an amino acid sequence TVSNRFS (SEQ ID NO: 17); and a CDR3 including an amino acid sequence SQSSHVPPT (SEQ ID NO: 18)). In one embodiment, the human anti-CD74 antibody or fragment thereof may include a heavy chain variable region of the human mAb which may include CDRs of a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). In another embodiment, the human anti-CD 74 antibody or fragment thereof may include the light and heavy chain variable and constant regions of a human antibody, where the huCD74 CDRs of the light chain variable region of the human anti-CD74 mAb may include a CDR1 having an amino acid sequence RSSQSLVHRNGNTYLH (SEQ ID NO: 16); a CDR2 having an amino acid sequence TVSNRFS (SEQ ID NO: 17); and a CDR3 having an amino acid sequence SQSSHVPPT (SEQ ID NO: 18); and where the heavy chain variable region of the human mAb may include CDRs of a heavy chain variable region of a murine anti-CD74 mAb (e.g., a CDR1 including an amino acid sequence NYGVN (SEQ ID NO: 19); a CDR2 including an amino acid sequence WINPNTGEPTFDDDFKG (SEQ ID NO: 20); and a CDR3 including an amino acid sequence SRGKNEAWFAY (SEQ ID NO: 21)). The human mAb or fragment thereof may include a human IgG1.

Multispecific and Multivalent Antibodies

The anti-CD74 binding molecule of the present immunoconjugates and compositions, as well as other binding molecules with different specificities for use in combination therapy, can also include multispecific antibodies (comprising at least one binding site to a CD74 epitope or antigen and at least one binding site to another epitope on CD74 or another antigen),and multivalent antibodies (comprising multiple binding sites to the same epitope or antigen), or the antibodies can be both multivalent and multispecific.

A preferred binding molecule of the present immunoconjugates or compositions is a fusion protein, which contains four or more Fvs, or Fab's of a humanized, chimeric, human or murine anti-CD74 mAb or fragment thereof as described herein. Additionally, another preferred antibody fusion protein contains one or more Fvs, or Fab's of the mAbs or fragments thereof of a humanized, chimeric, human or murine anti-CD74 mAb or fragment thereof as described herein, and one or more Fvs or Fab's from antibodies specific for another antigen that is specific for a tumor cell marker that is not a CD74 antigen. For example, the non-CD74 antigen may be expressed by the CD74-expressing cells and may include a tumor marker selected from a B-cell lineage antigen, (e.g., CD19, CD20, or CD22 for the treatment of B-cell malignancies). The non-CD74 antigen may also be expressed on other CD74 positive cells that cause other types of malignancies, such as S100 in melanoma, etc. Further, the tumor cell marker may be a non-B-cell lineage antigen selected from the group consisting of HLA-DR, CD30, CD33, CD52 MUC1 and TAC.

Also disclosed herein are bispecific or multispecific antibodies useful for preparing the disclosed immunoconjugates and compositions, where anti-CD74 mAbs or fragments thereof or antibody fusion proteins thereof are linked to an antibody or antibody fragment specific for a cancer marker substance, an epitope on the surface of an infectious disease organism, or a noxious substance in the blood or other body fluids. The bispecific and multispecific antibodies are particularly useful in the method of inducing clearance of a variety of noxious substances, where the bispecific antibody has at least one specificity for a noxious substance, such as a pathogenic organism, and at least one specificity for CD74, the HLA class-II invariant chain (Ii), as described in detail in U.S. Ser. No. 09/314,135, filed on May 19, 1999, entitled "Therapeutic Using a Bispecific Antibody," which is herein incorporated in its entirety by reference.

The immunoconjugates and compositions disclosed herein may also include an anti-CD74 multivalent antibody. This multivalent target binding protein may be constructed by association of a first and a second polypeptide. The first polypeptide comprises a first single chain Fv molecule covalently linked to a first immunoglobulin-like domain that preferably is an immunoglobulin light chain variable region domain. The second polypeptide comprises a second single chain Fv molecule covalently linked to a second immunoglobulin-like domain that preferably is an immunoglobulin heavy chain variable region domain. Each of the first and second single chain Fv molecules forms a target binding site, and the first and second immunoglobulin-like domains associate to form a third target binding site.

Diabodies, Triabodies and Tetrabodies

The immunoconjugates and compositions disclosed herein may also include functional bispecific single-chain antibodies (bscAb), also called diabodies. (See, e.g., Mack et al., *Proc. Natl. Acad. Sci.*, 92.: 7021-7025, 1995, incorporated herein by reference). For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into a eukaryotic expression vector. Functional protein expression can be obtained by transfecting the vector into Chinese Hamster Ovary cells. Bispecific fusion proteins are prepared in a similar manner. Bispecific single-chain antibodies and bispecific fusion proteins may be used to prepare the drug carriers.

For example, a humanized, chimeric or human anti-CD74 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized CD74 mAb connected to the $V_K$ polypeptide of the humanized CD74 mAb by a five amino acid residue linker are utilized. Each chain forms one half of the humanized CD74 diabody. In the case of triabodies, the three chains comprising $V_H$ polypeptide of the humanized CD74 MAb connected to the $V_K$ polypeptide of the humanized CD74 MAb by no linker are utilized. Each chain forms one third of the hCD74 triabody.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

Conjugated multivalent and multispecific anti-CD74 antibodies

In another embodiment, a conjugated multivalent anti-CD74 antibody may be used to prepare the immunoconjugate or composition. Additional amino acid residues may be added to either the N- or C-terminus of the first or the second polypeptide. The additional amino acid residues may comprise a peptide tag, a signal peptide, a cytokine, an enzyme (for example, a pro-drug activating enzyme), a hormone, a peptide toxin, such as pseudomonas exotoxin, a peptide drug, a cytotoxic protein or other functional proteins. As used herein, a functional protein is a protein that has a biological function.

In one embodiment, drugs, toxins, radioactive compounds, enzymes, hormones, cytotoxic proteins, chelates, cytokines and other functional agents may be conjugated to the multivalent target binding protein, preferably through covalent attachments to the side chains of the amino acid residues of the multivalent target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapeutic agent can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., *Proc. Natl. Acad. Sci. USA*, 75:3867-3870, 1978, U.S. Pat. Nos. 4,699,784 and 4,046,722, which are incorporated herein by reference. Conjugation preferably does not significantly affect the binding specificity or affinity of the multivalent binding protein.

Humanized, Chimeric and Human Antibodies Use for Treatment and Diagnosis

Humanized, chimeric and human monoclonal antibodies, i.e., anti-CD74 mAbs and other MAbs described herein, are suitable for use in the therapeutic methods and diagnostic methods which utilize immunoconjugates and compositions as described herein. Accordingly, the immunoconjugates or compositions may include naked humanized, chimeric and human antibodies or antibodies, which have been conjugated to a carrier, a therapeutic agent, or a diagnostic agent. The immunoconjugates may be administered as a multimodal therapy. For example, additional therapeutic or diagnostic agents may be administered before, simultaneously, or after administration of the immunoconjugate or composition.

The efficacy of the immunoconjugates may be enhanced by supplementing the anti-CD74 binding molecules with one or more other binding molecules, (i.e., mAbs to specific antigens, such as CD4, CD5, CD8, CD14, CD15, CD19, CD21, CD22, CD23, CD25, CD30, CD33, CD37, CD38, CD40, CD40L, CD46, CD52, CD54, CD80, CD126, B7, MUC1, Ia, tenascin, HM1.24, or HLA-DR, preferably mature HLA-DR dimer, with one or more immunoconjugates of anti-CD74, or antibodies to theses recited antigens). Preferred B-cell-associated antigens include those equivalent to human CD19, CD20, CD21, CD22, CD23, CD46, CD52, CD74, CD80, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD22, CD21, CD23, CD74, CD80, and HLA-DR antigens. Particularly preferred T-cell antigens are those equivalent to human CD4, CD8 and CD25 antigens. CD46 is an antigen on the surface of cancer cells that block complement-dependent lysis (CDC). Preferred malignant melanoma associated antigens are those equivalent to MART-1, TRP-1, TRP-2 and gp100. Further, preferred multiple myeloma-associated antigens are those equivalent to MUC1 and CD38.

The supplemental binding molecule may be naked or conjugated with a carrier, a therapeutic agent, or a diagnostic agent, including lipids, polyers, drugs, toxins, immunomodulators, hormones, enzymes, and therapeutic radionuclides, etc. The supplement binding molecule may be administered concurrently, sequentially, or according to a prescribed dosing regimen, with the anti-CD74 immunoconjugate.

Further, contemplating herein is the administration of an immunoconjugate for diagnostic and therapeutic uses in B cell lymphomas and other disease or disorders. An immunoconjugate, as described herein, is a molecule comprising a binding molecule conjugated to a carrier. The immunoconjugate may be used to form a composition that further includes a therapeutic or diagnostic agent, which may include a peptide that may bear the diagnostic or therapeutic agent. An immunoconjugate retains the immunoreactivity of the binding molecule, (i.e., the antibody moiety has about the same or slightly reduced ability to bind the cognate antigen after conjugation as before conjugation). Immunoconjugates may include binding molecule conjugated to any suitable second molecule, (e.g., lipids, proteins, carbohydrates, (which may form higher-ordered structures), or higher-ordered structures themselves, such as liposomes, micelles, and/or nanoparticles). To facilitate delivery of certain effectors, it may be desirable to conjugate an anti-CD74 antibody to one or more molecules that are capable of forming higher-ordered structures (e.g., amphiphilic lipids). Amphiphilic molecules may also be desirable to facilitate delivery of effectors that demonstrate limited solubility in aqueous solution.

A wide variety of diagnostic and therapeutic reagents can be advantageously used to form the immunoconjugates and compositions as described herein. Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and apoptotic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA can be conjugated to one or more components of the compositions as described herein. Alternatively, a suitable peptide including a detectable label, (e.g., a fluorescent molecule), or a cytotoxic agent, (e.g., a heavy metal or radionuclide), can be covalently, non-covalently, or other associated with more components of the compositions as described herein. For example, a therapeutically useful immunoconjugate can be obtained by incorporating a photoactive agent or dye in the composition as described herein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). Endoscopic applications are also contemplated. Endoscopic methods of detection-and therapy are described in U.S. Pat. Nos. 4,932, 412; 5,525,338; 5,716,595; 5,736,119; 5,922,302; 6,096,289; and 6,387,350, which are incorporated herein by reference in their entirety. Thus, contemplated herein is the therapeutic use of anti-CD74 immunoconjugate compositions comprising photoactive agents or dyes, and the present diagnostic/therapeutic methods may include the diagnostic or therapeutic use of anti-CD74 immunoconjugate compositions comprising photoactive agents or dyes.

Also contemplated is the use of radioactive and non-radioactive agents as diagnostic agents in the anti-CD74 immunoconjugate compositions as described herein. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies described herein. (See U.S. Ser. No. 09/921,290 filed on Oct. 10, 2001, which is incorporated in its entirety by reference).

Furthermore, the anti-CD74 immunoconjugate compositions may include a radioisotope or a positron-emitter useful for diagnostic imaging. Suitable radioisotopes may include those in the energy range of 60 to 4,000 keV. Suitable radioisotopes may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, $^{111}$In, $^{123}$I, $^{124}$I, $^{125}$I, $^{131}$I, and like. (See, e.g., U.S. patent application entitled "Labeling Targeting Agents with Gallium-68"- Inventors G. L. Griffiths and W. J. McBride, (U.S. Provisional Application No. 60/342,104), which discloses positron emitters, such as $^{18}$F, $^{68}$Ga, $^{94m}$Tc. and the like, for imaging purposes and which is incorporated in its entirety by reference).

A toxin, such as *Pseudomonas* exotoxin, may also be present in the anti-CD74 immunoconjugate compositions as described herein. For example, the toxin may be complexed to or form the therapeutic agent portion of an antibody fusion protein of an anti-CD74 antibody described herein. Other toxins include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. (See, e.g., Pastan et al., *Cell* 47:641 (1986), and Goldenberg, *CA—A Cancer Journal for Clinicians* 44:43 (1994). Additional toxins suitable for use herein are known to those of skill in the art and are disclosed in U.S. Pat. No. 6,077,499, which is incorporated in its entirety by reference).

An immunomodulator, such as a cytokine may also be present in the administered anti-CD74 immunoconjugate compositions as described herein. For example, an immunomodulator may be conjugated to, or form the therapeutic agent portion of an antibody fusion protein or be administered as part of the anti-CD74 immunoconjugate compositions as described herein. Suitable cytokines include, but are not limited to, interferons and interleukins, as described below.

Preparation of Immunoconjugates

The immunoconjugates described herein can be prepared by known methods of linking antibodies with lipids, carbohydrates, protein, or other atoms and molecules. For example, the binding molecules described herein can be conjugated with one or more of the carriers described herein (e.g., lipids, polymers, liposomes, micelles, or nanoparticles) to form an immunoconjugate, and the immunoconjugate can incorporate a therapeutic or diagnostic agent either covalently, non-covalently, or otherwise. Further, any of the binding molecules described herein can be further conjugated with one or more therapeutic or diagnostic agents described herein, or additional carriers. Generally, one therapeutic or diagnostic agent may be attached to each binding molecule but more than one therapeutic agent or diagnostic agent can be attached to the same binding molecule. The antibody fusion proteins contemplated herein comprise two or more antibodies or fragments thereof and each of the antibodies that comprises this fusion protein may be conjugated with one or more of the carriers described herein. Additionally, one or more of the antibodies of the antibody fusion protein may have one or more therapeutic of diagnostic agent attached. Further, the therapeutic do not need to be the same but can be different therapeutic agents. For example, the compositions described herein may include a drug and a radioisotope.

For example, an IgG can be radiolabeled with $^{131}$I and conjugated to a lipid, such that the IgG-lipid conjugate can form a liposome. The liposome may incorporate one or more therapeutic or diagnostic agents, (e.g., a drug such as FUdR-dO). Alternatively, in addition to the carrier, the IgG may be conjugated to $^{131}$I (e.g., at a tyrosine residue) and a drug (e.g., at the epsilon amino group of a lysine residue), and the carrier may incorporate an additional therapeutic or diagnostic agent. Therapeutic and diagnostic agents may be covalently associated with the binding molecule, (e.g., conjugated to reduced disulfide groups, carbohydrate side chains, or any other reactive group on the binding molecule.

A carrier, therapeutic agent, or diagnostic agent can be attached at the hinge region of a reduced antibody component via disulfide bond formation. As an alternative, peptides can be attached to an antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well known in the art. (See, e.g., Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995)). Alternatively, the carrier, therapeutic agent, or diagnostic agent can be conjugated via a carbohydrate moiety in the Fc region of an antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well known to those of skill in the art. (See, e.g., Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference). Similar chemistry can be used to conjugate one or more anti-CD74 binding molecules to one or more carriers, therapeutic agents, or diagnostic agents. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region may be absent if the anti-CD74 binding molecule is an antibody fragment. However, it is possible to introduce a carbohydrate moiety into the light chain variable region of a full-length antibody or antibody fragment. (See, e.g., Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference). The engineered carbohydrate moiety may be used to attach a carrier or a therapeutic or diagnostic agent.

Carriers (Lipids, Liposomes, Micelles, Polymers, and Nanoparticles)

The formation of liposomes and micelles is known in the art. (See, e.g., Wrobel et al., *Biochimica et Biophysica Acta*, 1235:296 (1995); Lundberg et al., *J. Pharm. Pharmacol.*, 51:1099-1105 (1999); Lundberg et al., *Int. J. Pharm.*, 205: 101-108 (2000); Lundberg, *J. Pharm. Sci.*, 83:72-75 (1994); Xu et al., *Molec. Cancer Ther.*, 1:337-346 (2002); Torchilin et al., *Proc. Nat'l. Acad. Sci.*, 100:6039-6044 (2003); U.S. Pat. Nos. 5,565,215; 6,379,698; and U.S. Pat. No. 2003/0082154). Nanoparticles or nanocapsules formed from polymers, silica, or metals, which are useful for drug delivery or imaging, have been described as well. (See, e.g., West et al., *Applications of Nanotechnology to Biotechnology*, 11:215-217 (2000); U.S. Pat. Nos. 5,620,708; 5,702,727; and U.S. Pat. No. 6,530,944).

Immunoliposomes

The conjugation of antibodies or binding molecules to liposomes to form a targeted carrier for therapeutic or diagnostic agents has been described. (See, e.g., Bendas, *Biodrugs*, 15:215-224 (2001); Xu et al., *Molec. Cancer Ther.*, 1:337-346 (2002); Torchilin et al., *Proc. Nat'l. Acad. Sci.*, 100:6039-6044 (2003); Bally, et al., *J. Liposome Res.*, 8:299-335 (1998); Lundberg, *Int. J. Pharm.*, 109:73-81 (1994); Lundberg, *J. Pharm. Pharmacol.*, 49:16-21 (1997); Lundberg, *Anti-cancer Drug Design*, 13:453-461 (1998)). See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

Pharmaceutically Acceptable Excipients

The immunoconjugates or compositions may include one or more pharmaceutically suitable excipients, one or more additional ingredients, or some combination of these.

The immunoconjugate or compositions disclosed herein can be formulated according to known methods to prepare pharmaceutically useful compositions, whereby the immunoconjugate or compositions are combined in a mixture with a pharmaceutically suitable excipient. Sterile phosphate-buffered saline is one example of a pharmaceutically suitable excipient. Other suitable excipients are well known to those in the art. (See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or compositions disclosed herein can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or compositions may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate or composition including the immunoconjugate that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, or composition including the immunoconjugate, is administered to a mammal in a therapeutically effective amount. A suitable subject for the therapeutic and diagnostic methods disclosed herein is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal.

Methods of Treatment

Contemplated herein is the use of immunoconjugates or compositions including immunoconjugates as the primary composition for treatment of a CD74 expressing malignancy, where the disease or disorder is selected from the group consisting of an immune dysregulation disease, an autoimmune disease, organ graft rejection, and graft versus host disease. The CD74 expressing malignancy is selected from the group consisting of a solid tumor, non-Hodgkin's lymphoma, Hodgkin's lymphoma, multiple myeloma, a B-cell malignancy and/or a T-cell malignancy. The solid tumor is selected from the group consisting of a melanoma, carcinoma and sarcoma and the carcinoma is selected from the group consisting of a renal carcinoma, lung carcinoma, intestinal carcinoma, stomach carcinoma and melanoma. The B-cell malignancy is selected from the group consisting of indolent forms of B-cell lymphomas, aggressive forms of B-cell lymphomas, chronic lymphatic leukemias, acute lymphatic leukemias, and multiple myeloma, B-cell disorders and other diseases. In particular, the compositions described herein are particularly useful for treatment of various autoimmune as well as indolent forms of B-cell lymphomas, aggressive forms of B-cell lymphomas, chronic lymphatic leukemias, acute lymphatic leukemias, multiple myeloma, and Waldenström's macroglobulinemia. For example, humanized anti-CD74 antibody components and immunoconjugates can be used to treat both indolent and aggressive forms of non-Hodgkin's lymphoma.

More specifically, the method for treating a B-cell malignancy may include administering to a subject with a B-cell related malignancy, a therapeutic composition comprising a pharmaceutically acceptable carrier, a therapeutic agent, and an immunoconjugate including an anti-CD74 binding molecule, (e.g., a humanized, chimeric, or human anti-CD74 mAb or fragment thereof or antibody fusion protein thereof), wherein the B-cell malignancy is a lymphoma or leukemia. More specifically, the B-cell malignancy is indolent forms of B-cell lymphomas, aggressive forms of B-cell lymphomas, multiple myeloma, chronic lymphatic leukemias, or acute lymphatic leukemias. The immunoconjugate or composition comprising the immunoconjugate is administered intravenously or intramuscularly at a dose of 20-2000 mg. The present method further comprises administering the immunoconjugate or composition before, simultaneously, or after the administration of at least one additional therapeutic agent or diagnostic agent used to treat the B-cell malignancy. The additional agent may include an additional immunoconjugate as described herein, including a therapeutic or diagnostic agent. A therapeutic agent may include a naked antibody, an immunomodulator, a hormone, a cytotoxic agent, an enzyme, and/or an antibody conjugated to at least one immunomodulator, radioactive label, hormone, enzyme, or cytotoxic agent, or a combination thereof. The immunomodulator preferably is a cytokine and the cytotoxic agent preferably is a drug or toxin. The antibody that is administered in combination as a naked antibody or as a supplemental immunoconjugate preferably is reactive with CD4, CD5, CD8, CD14, CD15, CD19, CD20, CD21, CD22, CD23, CD25, CD30, CD33, CD37, CD38, CD40, CD40L, CD46, CD52, CD54, CD80, CD126, B7, MUC2, MUC3, MUC4, Ia, HM1.24, tenascin, and HLA-DR, (preferably a mature HLA-DR dimer), VEGF, EGFR, CEA, CSAp, ILGF, placental growth factor, carbonic anhydrase IX, IL-6 or combinations thereof.

Also contemplated herein is the treatment of a malignancy comprising administering to a subject with a CD74 antigen-positive malignancy other than lymphoma or leukemia, a therapeutic composition that includes: (1) an immunoconjugate of an anti-CD74 binding molecule and a carrier; (2) an effector; and (3) a pharmaceutically acceptable excipient. The immunoconjugate or composition is administered intravenously or intramuscularly at a dose of 20-5000 mg. Further, the immunoconjugate may be administered before, simultaneously, or after the administration of at least one additional therapeutic agent or diagnostic agent. Therapeutic agents, as described above and throughout the specification, may include an immunomodulator, a hormone, a cytotoxic agent, or a binding molecule (either naked or conjugated to at least one immunomodulator, radioactive label, enzyme, hormone, cytotoxic agent, antisense oligonucleotide, or a combination thereof, where the immunomodulator preferably is a cytokine and the cytotoxic agent preferably is a drug or toxin). A therapeutic agent or diagnostic agent may include the compositions or immunoconjugates as disclosed herein. When an antibody is administered in combination with the therapeutic and/or diagnostic composition to treat a malignancy that is not a B-cell malignancy, it should be reactive with a tumor marker other than CD74, which is expressed by the cells that comprise the malignancy that is treated, and the antibody should be formulated in a pharmaceutically acceptable vehicle. Examples of antibodies that can be administered for malignant melanoma associated antigens are those antibodies reactive with MART-1, TRP-1, TRP-2 and gp100. Further, preferred antibodies to multiple myeloma-associated antigens are those reactive with MUC1 and CD38.

The compositions for treatment contain at least one immunoconjugate, which typically includes a humanized, chimeric or human monoclonal anti-CD74 antibody alone or in combination with other antibodies, such as other humanized, chimeric, or human antibodies. In particular, combination therapy wherein the immunoconjugate includes a fully human antibody is also contemplated.

The compositions also may include an immunomodulator as an effector. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-, -and-), the stem cell growth factor designated "S1 factor," erythropoietin, thrombopoietin or a combination thereof. Examples of suitable immunomodulator moieties include IL-1, IL-2, IL-3, IL-6, IL-10, IL-12, IL-18, IL-21, and a combination thereof, and interferon-, TNF-, and the like. The immunomodulator may be present in the composition, or alternatively, the immunomodulator can be administered before, simultaneously, or after administration of the therapeutic and/or diagnostic compositions. As discussed supra, the anti-CD74 antibody may also be conjugated to, the immunomodulator. The immunomodulator may also be conjugated to a hybrid antibody consisting of one or more antibodies binding to different antigens.

Multimodal therapies contemplated herein further include immunotherapy with immunoconjugates that include anti-CD74 binding molecules supplemented with administration of additional binding molecules, (e.g., anti-CD22, anti-CD19, anti-CD21, anti-CD20, anti-CD80, anti-CD23, anti-CD46 or HLA-DR, preferably the mature HLA-DR dimer antibodies in the form of naked antibodies, fusion proteins, or as immunoconjugates). Further, a micelle, liposome, or nanoparticle, as described herein, may include binding molecules in addition to anti-CD74 binding molecules. Useful antibodies may be polyclonal, monoclonal, chimeric, human or humanized antibodies that recognize at least one epitope on the above-noted antigenic determinants. For example, anti-CD19 and anti-CD22 antibodies are known to those of skill in the art. (See, e.g., Ghetie et al., Cancer Res. 48:2610 (1988); Hekman et al., Cancer Immunol. Immunother. 32:364 (1991); Longo, Curr. Opin. Oncol. 8:353 (1996) and U.S. Pat. Nos. 5,798,554 and 6,187,287, incorporated in their entirety by reference.)

In another form of multimodal therapy, subjects receive anti-CD74 immunoconjugates, in conjunction with standard cancer chemotherapy. For example, "CVB" (1.5 $g/m^2$ cyclophosphamide, 200-400 $mg/m^2$ etoposide, and 150-200 $mg/m^2$ carmustine) is a regimen used to treat non-Hodgkin's lymphoma. Patti et al., Eur. J. Haematol. 51: 18 (1993). Other suitable combination chemotherapeutic regimens are well known to those of skill in the art. (See, e.g., Freedman et al., "Non-Hodgkin's Lymphomas," in CANCER MEDICINE, VOLUME 2, 3rd Edition, Holland et al. (eds.), pages 2028-

2068 (Lea & Febiger 1993)). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second-generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and bryostatin-1. In a preferred multimodal therapy, both chemotherapeutic drugs and cytokines are co-administered with an antibody, immunoconjugate or fusion protein. The cytokines, chemotherapeutic drugs and antibody or immunoconjugate can be administered in any order, or together.

In a preferred embodiment, NHL is treated with 4 weekly infusions of the humanized anti-CD74 immunoconjugate (e.g., a therapeutic emulsion) at a dose of 200-400 mg/m$^2$ weekly for 4 consecutive weeks or every-other week (iv over 2-8 hours), repeated as needed over next months/yrs. Also preferred, NHL is treated with 4 semi-monthly infusions as above, but combined with epratuzumAb (anti-CD22 humanized antibody) on the same days, at a dose of 360 mg/m$^2$, given as an iv infusion over 1 hour, either before, during or after the anti-CD74 immunoconjugate infusion. Still preferred, NHL is treated with 4 weekly infusions of the anti-CD74 immunoconjugate as above, combined with one or more injections of CD22 mAb radiolabeled with a therapeutic isotope such as yttrium-90 (at dose of $^{90}$Y between 5 and 35 mCi/meter-square as one or more injections over a period of weeks or months.

In addition, a therapeutic composition as contemplated herein can contain a mixture or hybrid molecules of monoclonal anti-CD74 immunoconjugates directed to different, non-blocking CD74 epitopes. Accordingly, contemplated herein are therapeutic compositions comprising a mixture of monoclonal anti-CD74 immunoconjugates that bind at least two CD74 epitopes. Additionally, the immunoconjugates described herein may contain a mixture of anti-CD74 antibodies with varying CDR sequences.

As discussed supra, the immunoconjugates can be used for treating B cell lymphoma and leukemia, and other B cell diseases or disorders as well as other malignancies in which affected or associated malignant cells are reactive with CD74. For example, anti-CD74 immunoconjugates can be used to treat immune dysregulation disease and related autoimmune diseases, including Class-III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

In particular, immunoconjugates including humanized, chimeric or human anti-CD74 mAbs or fragments thereof or antibody fusion proteins thereof are administered to a subject with one or more of these autoimmune diseases. The anti-CD74 immunoconjugates disclosed herein are particularly useful in the method of treating autoimmune disorders, disclosed in pending U.S. Ser. No. 09/590,284 filed on Jun. 9, 2000 entitled "Immunotherapy of Autoimmune Disorders using Antibodies that Target B-Cells," which is incorporated in its entirety by reference. Preferably the anti-CD74 immunoconjugate is administered intravenously or intramuscularly at a dose of 20-5000 mg. Further, the anti-CD74 immunoconjugate is administered before, during or after the administration of at least one therapeutic agent or diagnostic agent. The therapeutic agent, as described above and throughout the specification, may include an antibody, an immunomodulator, a hormone, an enzyme, a cytotoxic agent, an antibody conjugated to at least one immunomodulator, radioactive label, hormone, enzyme, or cytotoxic agent, antisense oligonucleotide or a combination thereof, where the immunomodulator is a cytokine and said cytotoxic agent is a drug or toxin. The therapeutic agent may include an immunoconjugate as described herein. Antibodies that may be administered in combination as a naked antibody or as a supplemental immunoconjugate include antibodies that react with CD4, CD5, CD8, CD14, CD15, CD19, CD20, CD21, CD22, CD23, CD25, CD30, CD33, CD37, CD38, CD40, CD40L, CD46, CD52, CD54, CD80, CD126, B7, MUC1, Ia, HM1.24, tenascin, and mature HLA-DR, preferably a mature HLA-DR dimer, formulated in a pharmaceutically acceptable vehicle.

Method of Diagnosis

Also provided is a method of diagnosing a disease in a subject, diagnosed with or suspected of having at least one of the diseases selected from the groups consisting of lymphoma, leukemia, myeloma, other CD-74-expressing malignancies, immune dysregulation disease, autoimmune disease and a combination thereof, comprising administering to said subject a diagnostically effective amount of a composition that includes (1) an immunoconjugate including at least one anti-CD74 binding molecule conjugated to a carrier, (2) a diagnostic agent, and (3) a pharmaceutically acceptable excipient. The diagnostic agent may be covalently, non-covalently, or otherwise associated with one or more components of the composition. A useful diagnostic agent may include a radioisotope, wherein the photons of the radioisotope are detected by radioscintigraphy or PET, or a metal that can be detected by MRI, or a liposome or gas filled liposome, and wherein the liposome can be detected by an ultrasound scanning device. As such, the immunoconjugate may form a liposome, and/or the diagnostic agent may comprise a second liposome.

The internalization of the immunoconjugate into target cells can be followed by fluorescence labeling, essentially according to the procedure of Pirker et al., *J. Clin. Invest.*, 76: 1261 (1985), which is incorporated by reference.

In a related vein, a method for screening/diagnosing bone cancers is described in Juweid et al., 1999, could benefit from the immunoconjugates disclosed herein. Accordingly, a method comprising $^{99m}$Tc-labeled humanized or chimeric anti-CD74 mAb immunoconjugates is contemplated.

EXAMPLES

Example 1

Preparation of Anti-CD74 Immunoliposomes Carrying FUdR-dO

Triolein (TO), egg phosphatidylcholine (EPC), dipalmitoyl phosphatidylethanolamine (DPPE), cholesterol (CHOL), 8-hydroxy-1,3,6-pyrenetrisulfonate (HPTS), polyoxyethylenesorbitan monooleate (sorbitan 80), methoxypolyethyleneglycol (mean mol. wt 2000), oleoyl chloride, 3-(4,5-dimethylthiazol-2-yl)-2,5-diphenyltetrazolium bromide (MTT) and DL-dithiotreitol (DTT) were obtained from Sigma Chemical Co. (St. Louis, Mo.). Poly(ethylene glycol)-maleimide-N-hydroxy-succinimidyl ester (MAL-PEG$_{2000}$-NHS) was purchased from Shearwater Polymers Europe (Enschede, The Netherlands). [$^3$H]Cholesteryl oleoyl ether (COE) and [$^{14}$C]dipalmitoyl phosphatidylcholine were obtained from Amersham International plc (Amersham, UK). A PEG$_{2000}$ derivative of DPPE with a maleimide group at the distal terminus of the PEG chain (DPPE-PEG-MAL) was synthesized by reacting 25 µmol NHS-PEG-MAL with 23 µmol DPPE and 50 µmol triethylamine in chloroform for 6 h at 40° C. The product was purified by preparative silica gel TLC. 3',5'-O-dioleoyl-FUdR (FUdR-dO) was synthesized by adding 20 µmol oleoyl chloride and 50 µl N,N-diisopropylethylamine to 10 µmol FUdR in dimethylacetamide. The mixture was incubated overnight at 40° C. and then water was added to the mixture and the fatty acid derivative of FUdR was extracted with chloroform. The prodrug was purified by preparative silica gel TLC with chloroform/methanol (95:5) as eluent.

The Burkitt's lymphoma cell lines, Raji and Ramos, Jurkat acute lymphoblastic leukemia T-cells and HL-60 myelomonocytic leukemia cells, obtained from American Type Culture Collection (Rockville, Md.), were grown in RPMI 1640 medium with 10% heat-inactivated fetal calf serum. Cells were maintained at 37° C. and gassed with 5% CO$_2$ in air.

The anti-CD74 Ab, LL1, was obtained from Immunomedics, Inc. (Morris Plains, N.J.). It was labeled with fluorescein (FITC) for quantitation.

Submicron lipid emulsions were prepared as described in detail elsewhere. (See, Lundberg, *J. Pharm. Sci.*, 83:72-75 (1994); Lundberg et al., *Int. J. Pharm.*, 134:119-127 (1996)). The composition of the drug-loaded emulsions was TO, EPC, polysorbate 80, DPPE-PEG$_{2000}$-MAL, FUdR-dO 2:2:0.8:0.6:0.3 (w/w). The components were dispensed into vials from stock solutions and the solvent was evaporated to dryness under reduced pressure. Phosphate-buffered saline (PBS) was added and the mixture was heated to 50° C., vortex mixed for 30 s, and sonicated with a Branson probe sonicator for 2 min.

Drug loaded liposomes were composed of EPC, DPPE-PEG$_{2000}$-MAL, FUdR-dO 1:0.2:0.1 (w/w). In experiments involving HPTS-encapsulated liposomes the composition was EPC, CHOL, DPPE-PEG2000-MAL 2:0.5:0.4. When required, the lipid drug-carriers were labeled with trace amounts of [$^3$H]COE. Dried lipid films were hydrated in 25 mM HEPES and 140 mM NaCl buffer (pH 7.4), (containing 35 mM HPTS when appropriate) subjected to five freezing-thawing cycles and subsequent sonication for 2 min with a Branson probe sonicator. The phospholipid concentration was quantitated by [$^{14}$C]DPPC. MAL 2:0.5:0.4. Coupling of LL1 to lipid drug-carriers was performed by reaction between the maleimide (MAL) groups at the distal PEG termini on the surface of the carriers and free thiol groups on the Ab. Before the coupling reaction LL1 was reduced with 50 mM dithiotreitol for 1 h at 4° C. in 0.2 M tris buffer (pH6.5). The reduced Ab was separated from excess dithiotreitol by use of Sephadex G-25 spin-columns, equilibrated with 50 mM sodium acetate buffered 0.9% saline (pH 5.3). The conjugation was performed in HEPES-buffered saline (pH 7.4) for 16 h at room temperature under argon. Excess maleimide groups were blocked with 2 mM 2-mercaptoethanol for 30 min, whereafter excess Ab and 2-mercaptoethanol were removed on a Sepharose CL-4B column. The immunoliposomes were collected near the void volume of the column, passed through a 0.22 µm sterile filter and stored at 4° C. The coupling efficiency was estimated by use of fluorescein labeled LL1.

Example 2

Cellular Uptake and Metabolism of the Anti-CD74 Immunoliposomes

Lipid drug-carriers containing the non-exchangeable marker [$^3$H]COE were used to study the cellular uptake of drug carrier. After completed incubation, the cells were thoroughly washed three times with cold PBS and the radioactivity measured by liquid-scintillation counting. The pH-sensitive probe HPTS was used to study the internalization of liposomes to low pH compartments. HPTS exhibits two major fluorescence excitation maxima: a peak at 403 maximal at low pH values and a peak at 454 maximal at high pH values, while the fluorescence is independent of pH at 413 nm (isobestic point). (See, Straubinger, et al., *Biochemistry*, 29:4929-4939 (1990)). The ratio between the fluorescence at 454 nm and 413 nm can be used to study the internalization of the HPTS-liposomes to intracellular acidic compartments. HPTS-liposomes were diluted to 80 µM phospholipid in HEPES buffer and added to culture dishes (4×10$^6$ cells) at 37° C. After incubation for 6 h the cells were washed twice with cold PBS and the fluorescence was measured in a stirred cuvette at 20° C. Peak heights were measured at 510 nm emission at the two excitation wavelengths (413 and 454 nm) and corrected for appropriate background fluorescence.

FIG. 5 demonstrates the concentration-dependent cellular association of lipid drug-carriers with coupled LL1 and lipid drug-carriers without coupled LL1. Association of lipid drug-carriers with and without coupled LL1 was concentration dependent. FIG. 5 shows that the Burkitt's lymphoma cells, Raji, show a massive interaction with LL1-lipid drug-carrier complexes as compared to untargeted preparations. LL1-emulsion conjugates, labeled with the nontransferable compound [$^3$H]COE, were taken up about 50 times faster than unconjugated emulsions by Raji cells in culture. The fast and massive uptake of immunoemulsions is demonstrated by the fact that under standard incubation conditions about 30% of the added preparation was associated with cells after 24 h. The corresponding association of emulsions without coupled Ab was about 0.6%. The uptake values for Ramos cells were considerably lower but still about 30 times higher for LL1-complexes than for uncomplexed emulsions. The time-dependent association of targeted carriers was fairly linear up to 24-h, but at prolonged incubation times the curve declined.

Example 3

Specificity of Immunoconjugates

Figure 6:
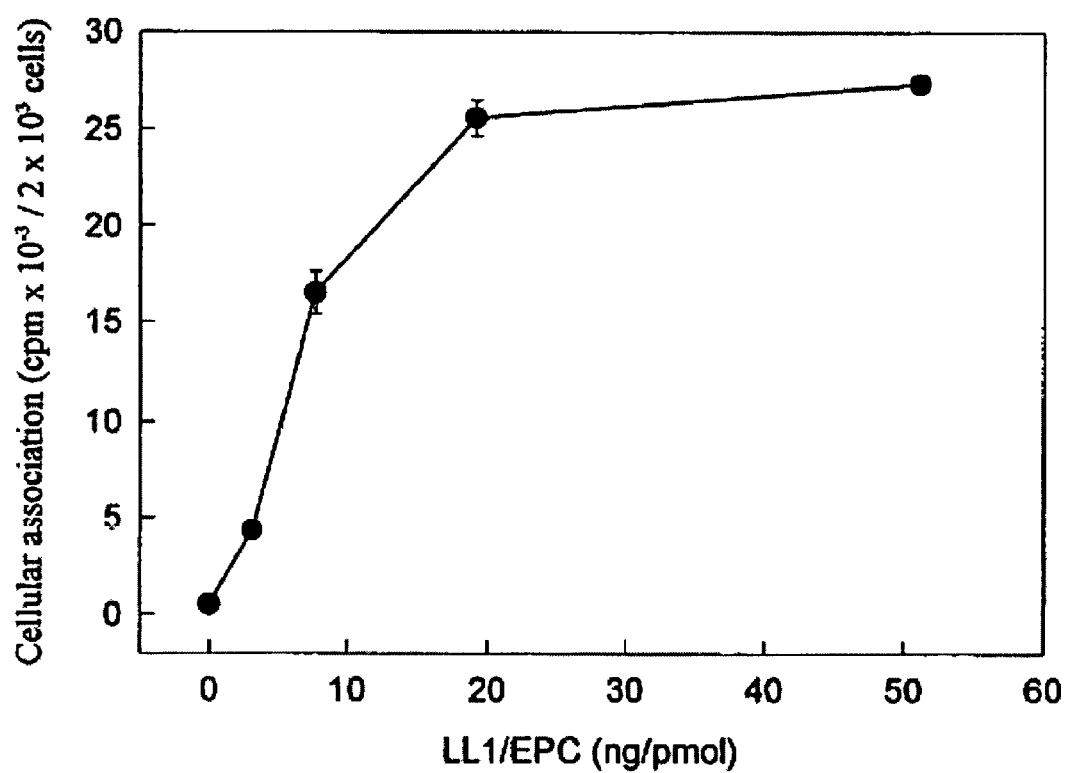
FIG. 6. Cellular association of [$^3$H]COE-labeled LL1-emulsions versus amount of LL1 per emulsion egg phosphatidylcholine (EPC) during a 24-h incubation at 37° C. (Mean±SE, n=4).
Figure 7:
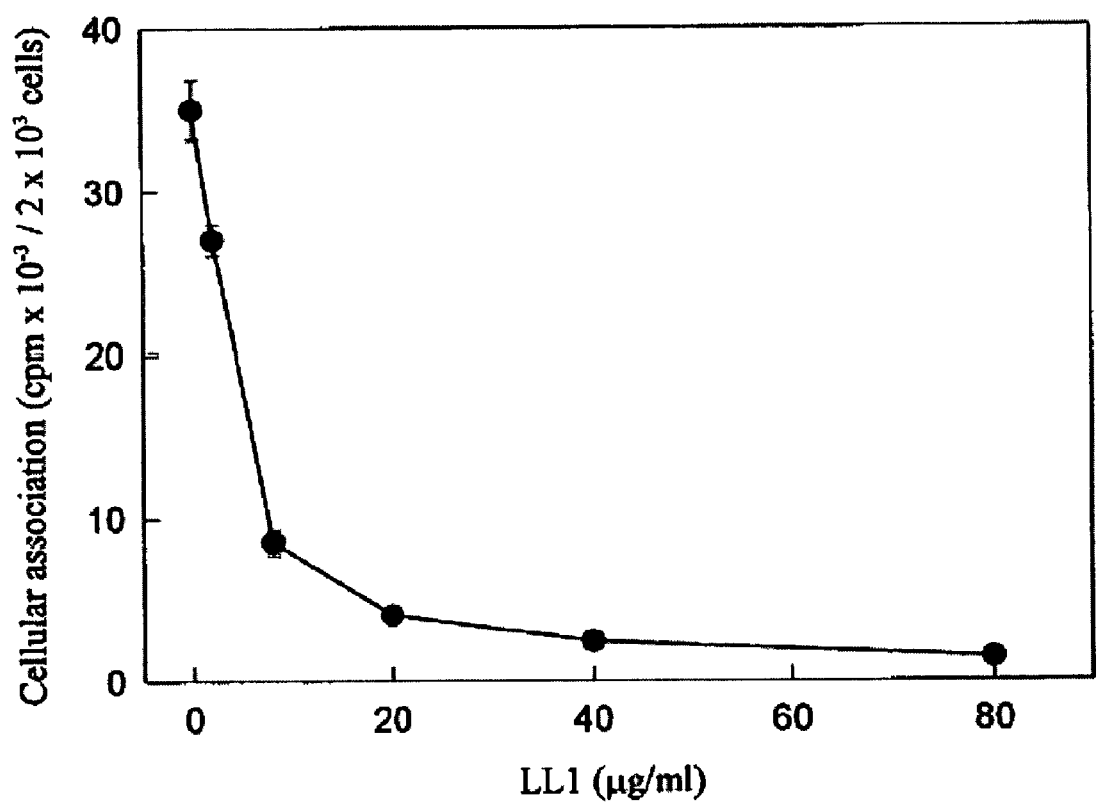
FIG. 7. Displacement curve for the association of [$^3$H] COE-labeled LL1-emulsions in the presence of different concentrations of free LL1. (Mean±SE, n=4).

The cell specificity of the preparations was tested on HL-60 and Jurkat cells. See FIG. 5, B. Bottom panel. The cellular association obtained after 24 h was between 1 and 2% for both cell types with no evident difference between conjugates and plain emulsions. This extent of cellular association clearly represent unspecific uptake. The specificity of the interaction was further studied by measuring the cellular association of [$^3$H]COE-labeled LL1-emulsions versus the amount of LL1 per emulsion EPC. See FIG. 6. These experiments demonstrated that association of the LL1-emulsions was dependent on the concentration of LL1. The specificity of the interaction of immunoemulsions with cells was also studied by displacement experiments. FIG. 7 shows that free LL1 competes effectively with the LL1-emulsion complexes and at high concentrations the cellular association is practically abolished. These findings strongly indicates that LL1 preserves its immunoreactivity after binding to lipid drug-carriers.

Example 4

Endocytosis of HPTS-containing Immunoliposomes

Figure 8:
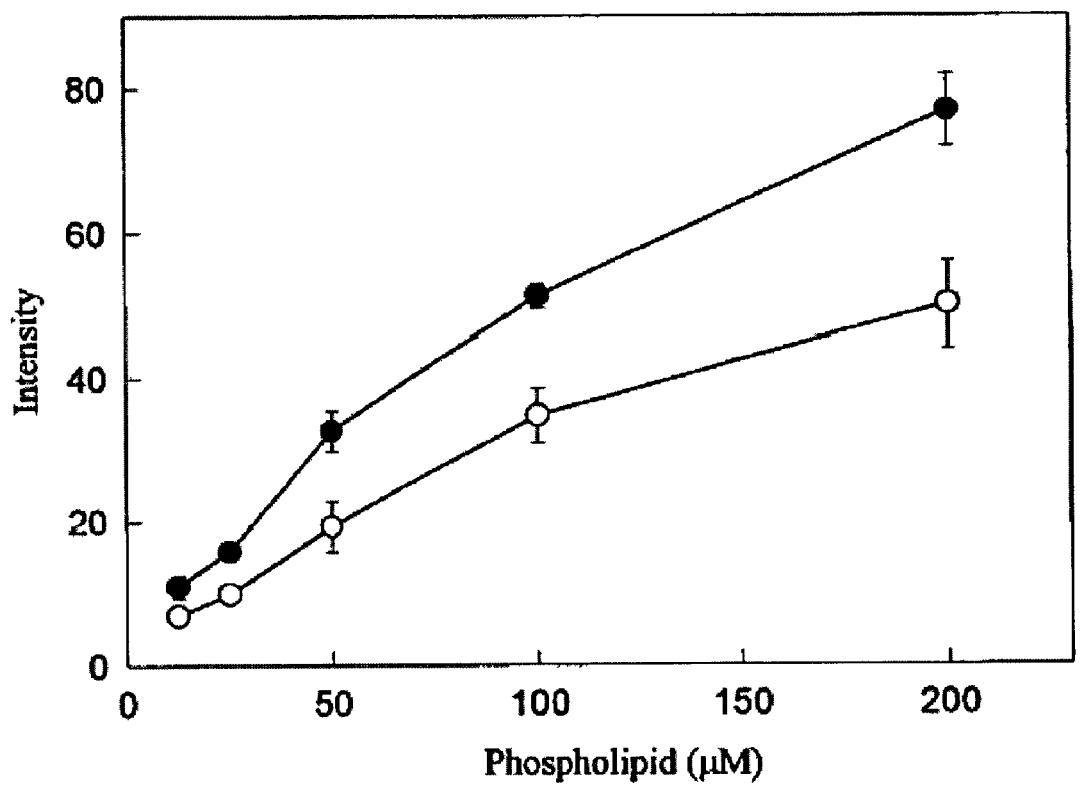
FIG. 8. Concentration-dependent association of 8-hydroxy-1,3,6-pyrenetrisulfonate (HPTS)-containing LL1-liposomes during a 6-h incubation at 37° C., measured at λ=413 nm (●) and λ=454 nm (○). (Mean±SE, n=3).

The intracellular fate of LL1-liposomal complexes was studied by use of the pH-sensitive probe HPTS. The spectral shifts of the probe with changes in pH make it a useful marker of the uptake and fate of the encapsulated dye. FIG. 8 shows the concentration-dependent cellular association of HPTS loaded LL1-liposomes. Internalization of LL1-liposomes to low-pH compartments was demonstrated by the fluorescence ratio $\lambda_{ex}$ 454/413. Values near 0.6 were obtained which corresponds to a pH value of 6.5. This value is near those obtained by other authors with HPTS-immunoliposomes. See Kirpotin, et al., *Biochemistry* 36 (1997) 66-75; Lopes de Menezes, et al., *J. Liposome Res.* 9 (1999) 199-228. HPTS-liposomes without ligand give values near 0.8, which corresponds to a pH value of about 7.0. See Lundberg, et al., *Int. J. Pharm.* 205 (2000) 101-108. It thus seems very likely that the LL1-drug-carrier complexes are delivered to and catabolized by the lysosomes.

Example 5

Cytotoxicity Assays

Comparison of the in vitro cytotoxicity of free FUdR and FUdR-dO-loaded emulsions and liposomes with and without coupled LL1 was performed on Raji human B-cell lymphoma lines with a proliferation assay utilizing tetrazolium dye, MTT. (See, Mosmann, *J. Immun. Meth.*, 65:55-63 (1983)). To begin, $4\times10^5$ cells were plated in 24-well plates and incubated with drug containing preparations. Control experiments included free LL1 and drug free emulsions and liposomes. Cells were incubated for 24 h at 37° C. in an atmosphere of 95% humidity and 5% $CO_2$. At the 24 h time point, the cells were washed twice before replacing with fresh media and incubated for an additional 48 h. At the end of the incubation time, tetrazolium dye was added, the formed reduction product was spun down, dissolved in EtOH:DMSO 1:1 and read at 570 nm.

Figure 9:
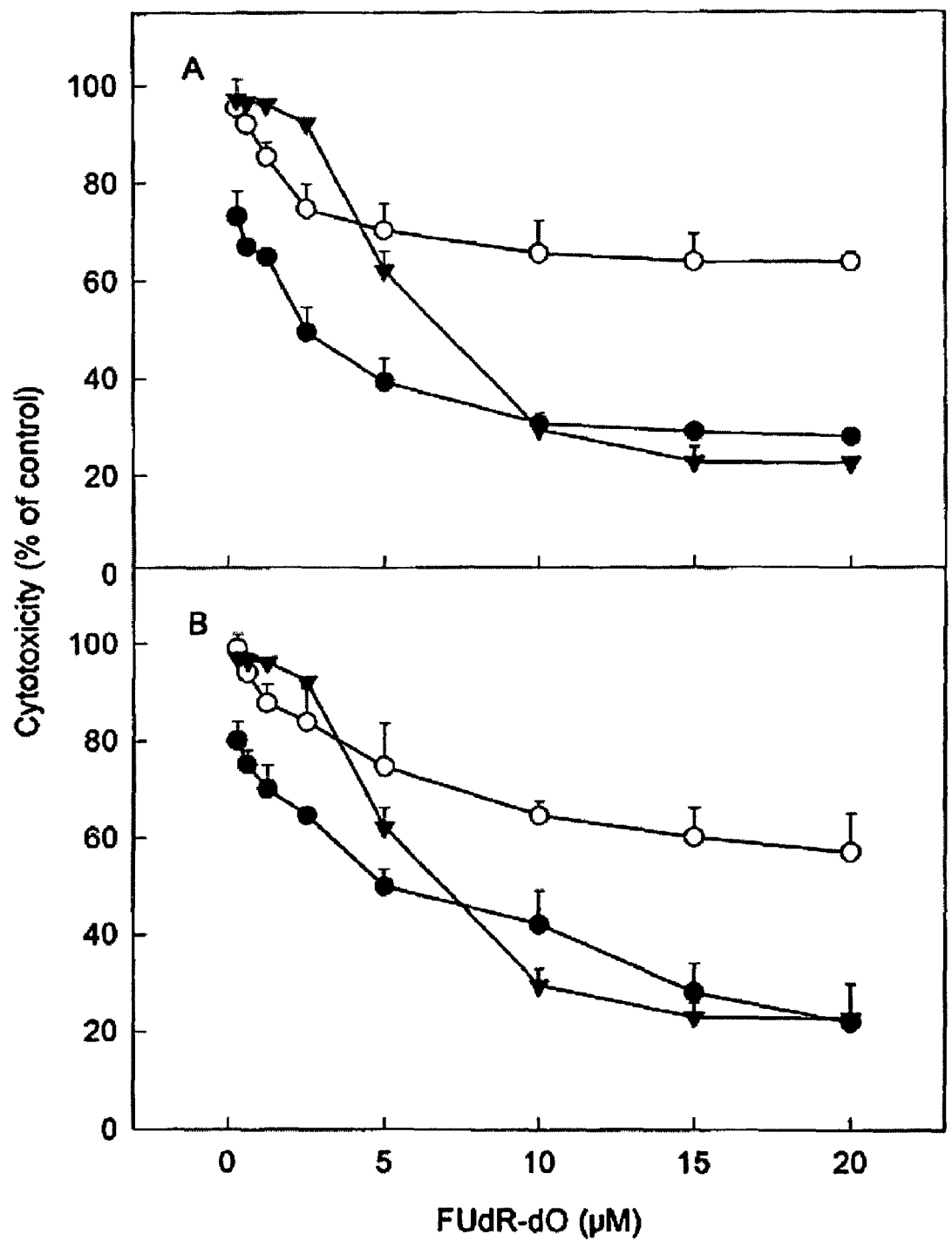
FIG. 9. Dose-response curves for FUdR-dO. A. Top panel. Raji lymphoma cells were treated with LL1-conjugated emulsions containing FUdR-dO (●); unconjugated emulsions containing FUdR-dO (○); or free FUdR in PBS as a comparison (▼). B. Bottom panel. Raji lymphoma cells were treated with LL1-conjugated liposomes containing FUdR-dO ( ); unconjugated liposomes containing FUdR-dO (○); or free FUdR in PBS as a comparison (▼). (Mean±SE, n=4).

The cytotoxic activity of FUdR-dO in LL1 conjugated emulsions and liposomes was tested and compared with the activity of unconjugated drug-carriers on Raji lymphoma cells. See FIG. 9. The effect of free FUdR (in PBS) was also recorded. The cells were incubated with the various preparations for 24-h, followed by an additional 48-h in fresh medium. From the dose-response curves it could be seen that FUdR-dO is somewhat more efficacious in emulsions than in liposomes. However, the activity of FUdR-dO administered in both LL1-emulsions and LL1-liposomes exceeded that of FUdR. The IC70 values obtained were 0.45, 1.25, 5.3 and 7.3 µM for FUdR-dO loaded LL1-emulsions, LL1-liposomes, emulsions and liposomes, respectively. The corresponding value for FUdR was calculated to 4.35 µM. The $IC_{50}$ values were 2.5, 5.3 and 7.0 µM for LL1-emulsions, LL1-liposomes and FudR, respectively (FUdR-dO in plain emulsions and liposomes did not reach that level).

The prodrug FUdR-dO employed in this study shows several advantageous features for administration in lipid drug-carriers. It is amphiphilic and will be situated in the phospholipid monolayer and bilayer of lipid emulsions and liposomes, respectively. This makes the preparation of drug-carrier very convenient; the components are just mixed together and sonicated. An alternative method, which is more suited for large scale production, would be the use of high pressure homogenization.

A prerequisite for site-specific delivery of the prodrug to the target cells is the stable entrapment of the prodrug in the drug-carrier. The unspecific transfer of FUdR-dO from carrier to cells was not actually measured but the much higher cytotoxic activity of the LL1-conjugated preparations indicates that the unspecific transfer of prodrug to cells is relatively low. That some degree of surface transfer probably occurs find support by a study of Koning et al., *Biochim. Biophys. Acta* 1420 (1999) 153-167. They found that dipalmitoyl-FUdR immunoliposomes, without internalization, could deliver the prodrug to target cells more efficient than liposomes without antibody.

The prodrug concept comprises a pharmacologically inactive compound that is activated when exposed into the target cells. In this respect FUdR-dO may fulfill the criteria of a good prodrug. It has been shown that FUdR fatty acid esters are hydrolyzed fast in cells, apparently in lysosomes. See id. An efficient intracellular liberation of the parent drug FUdR is also indirectly supported by the high cytotoxic efficacy of the FUdR-dO preparations.

This in vitro study demonstrates the potential for site-specific delivery of anti-cancer drugs by use of lipid drug-carriers with LL1 as targeting ligand. Several recent studies also show that lipid drug-carriers, even without attached ligand, can give in vivo advantage as administration vehicles for lipophilic and amphiphilic drugs. See Constantinides et al., *Pharm. Res.* 17 (2000) 175-182; Perkins et al., *Int. J. Pharm.* 200 (2000) 27-39; Bom et al., J. Controlled Release 74 (2001) 325-333; and Maranhao et al., *Cancer. Chemother. Pharmacol.* 49 (2002) 487-498.

An explanation for such an favorable effect appears to be that the half-life of the drug increases and the tolerability is improved so that high doses can be administered. A recent in vivo study with nude mice demonstrated specific Ab localization of LL1 to Ramos xenografts. See Shih et al., *Cancer Immunol. Immunother.* 49 (2000) 208-216. The present study shows an improved cytotoxic activity of the targeted prodrug compared to the parent drug. Immunoliposomes generally show lower or similar activity compared to the untargeted drug, but still demonstrate improved efficacy in in vivo experiments. See Moase et al., *Biochim. Biophys. Acta* 1510 (2001) 43-55; Lopes de Menezes et al., *Cancer Res.* 58 (1998) 3320-3330.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. For example, a variety of different binding pairs can be utilized, as well as a variety of different therapeutic and diagnostic agents. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

---

The invention claimed is:

1. A method for treating a disease or disorder comprising administering to a patient a therapeutic composition comprising
   (i) one or more anti-CD74 antibodies or antigen-binding fragments thereof reactive with the epitope of CD74 to which the LL1 antibody binds,
      wherein the anti-CD74 antibodies or antigen-binding fragments thereof are covalently bound to the PEG component of a PEG-lipid conjugate incorporated into a liposome;
      wherein one or more effectors are incorporated into the liposome in unmodified active form, or covalently bound to the lipid component of the liposome, or covalently bound to the PEG component of the liposome;
      wherein said anti-CD74 antibodies are chimeric, human or humanized;
      wherein the anti-CD74 antibody or antigen-binding fragment thereof is an anti-CD74 diabody, a triabody, tetrabody or an scFv, and,
   (ii) a pharmaceutically acceptable excipient,
      wherein the cells of the patient that are associated with the disease or disorder are CD74-expressing cells.

2. The method of claim 1, wherein the disease or disorder is a CD74-expressing malignancy.

3. The method of claim 1, wherein the disease or disorder is selected from the group consisting of an immune dysregulation disease, an autoimmune disease, an organ-graft rejection, and a graft-versus-host disease.

4. The method of claim 2, wherein the CD74-expressing malignancy is selected from the group consisting of a solid tumor, non-Hodgkin's lymphoma, Hodgkin's lymphoma, multiple myeloma, a B-cell malignancy, and a T-cell malignancy.

5. The method of claim 1, wherein the disease or disorder is a CD74-expressing malignancy other than lymphoma or leukemia.

6. The method of claim 2, wherein the CD74-expressing malignancy is a solid tumor.

7. The method of claim 6, wherein the solid tumor is selected from the group consisting of a melanoma, carcinoma, sarcoma, and glioma.

8. The method of claim 7, wherein the carcinoma is selected from the group consisting of a renal carcinoma, lung carcinoma, intestinal carcinoma, stomach carcinoma, breast carcinoma, prostate cancer, ovarian cancer, and melanoma.

9. The method of claim 2, wherein the CD74-expressing malignancy is a B-cell malignancy selected from the group consisting of indolent forms of B-cell lymphomas, aggressive forms of B-cell lymphomas, chronic lymphatic leukemias, acute lymphatic leukemias, and multiple myeloma.

10. The method of claim 1, wherein the composition is administered intravenously or intramuscularly at a dose of 20-5000 mg.

11. The method of claim 1, wherein the composition comprises LL1, or a fragment thereof.

12. The method of claim 1, wherein the composition further comprises one or more additional antibodies or fragments thereof selected from the group consisting of anti-CD19, anti-CD20, anti-CD22, anti-CD30, anti-CD33, anti-CD52, anti-HLA-DR, anti-MUC1, anti-TAC, and mixtures thereof.

13. The method of claim 12, wherein one or more of the additional antibodies are conjugated to one or more of the lipids, polymeric carriers, micelles, nanoparticles, or combinations thereof.

14. The method of claim 1, wherein the effector molecule comprises one or more drugs, prodrugs, toxins, enzymes, radioisotopes, immunomodulators, cytokines, hormones, antibodies, oligonucleotides, or combinations thereof.

15. The method of claim 1, wherein the effector comprises FUdR, FUdR-dO, or mixtures thereof.

16. The method of claim 1, wherein the composition further comprises one or more hard acid chelators or soft acid chelators.

17. The method of claim 1, wherein the composition further comprises cations selected from Group II, Group III, Group IV, Group V, transition, lanthanide or actinide metal cations, or mixtures thereof.

18. The method of claim 1, wherein the composition further comprises cations selected from Tc, Re, Bi, Cu, As, Ag, Au, At, Pb, or mixtures thereof.

19. The method of claim 1, wherein the composition further comprises NOTA, DOTA, DTPA, TETA, Tscg-Cys, Tsca-Cys, or mixtures thereof.

20. The method of claim 1, wherein the composition comprises a radionuclide.

21. The method of claim 20, wherein the radionuclide comprises 18F, 32P, 33P, 45Ti, 47Sc, 52Fe, 59Fe, 62Cu, 64Cu, 67Cu, 67Ga, 68Ga, 75Se, 77As, 89Y, 89Sr, 89Zr, 90Y, 94Tc, 94mTc, 99Mo, 99mTc, 105Pd, 105Rh, 111Ag, 111In, 123I, 124I, 125I, 131I, 142Pr, 143Pr, 149Pm, 153Sm, 154-158Gd, 161Tb, 166Dy, 166Ho, 166Ho, 169Er, 175Lu, 177Lu, 186Re, 188Re, 189Re, 194Ir, 198Au, 199Au, 211At, 211Pb 212Bi, 212Pb, 213Bi, 223Ra, 225Ac, or mixtures thereof.

22. The method of claim 20, wherein the composition comprises an enzyme.

23. The method of claim 22, wherein the enzyme comprises carboxylesterases, glucoronidases, carboxypeptidases, beta-lactamases, phosphatases, or mixtures thereof.

24. The method of claim 20, wherein the composition comprises an immunomodulator.

25. The method of claim 24, wherein the immunomodulator comprises IL-1, IL-2, IL-3, IL-6, IL-10, IL-12, IL-18, IL-21, interferon-α, interferon-β, interferon-γ, G-CSF, GM-CSF, or mixtures thereof.

26. The method of claim 1, wherein the composition comprises one or more agents for photodynamic therapy.

27. The method of claim 26, wherein the agent for photodynamic therapy is a photosensitizer.

28. The method of claim 27, wherein the photosensitizer comprises a benzoporphyrin monoacid ring A (BDP-MA), tin etiopurpurin (SnET2), sulfonated aluminum phthalocyanine (AISPc) or lutetium texaphyrin (Lutex).

29. The method of claim 1, wherein the composition comprises one or more diagnostic agents.

30. The method of claim 1, wherein the composition comprises a diagnostic radionuclide.

31. The method of claim 30, wherein the diagnostic radionuclide comprises 18F, 52Fe, 62Cu, 64Cu, 67Cu, 67Ga, 68Ga, 86Y, 89Zr, 94Tc, 94mTc, 94mTc, 99mTc, 111In, 123I, 124I, 125I, 131I, or mixtures thereof.

32. The method of claim 31, wherein the diagnostic radionuclide emits 25-4000 keV gamma particles and/or positrons.

33. The method of claim 29, wherein the diagnostic agent is used for performing positron emission tomography (PET).

34. The method of claim 1, further comprising performing positron-emission tomography (PET).

35. The method of claim 29, wherein the diagnostic agent comprises one or more image enhancing agents and the method further comprises performing magnetic resonance imaging (MRI).

36. The method of claim 35, wherein the image enhancing agent comprises gadolinium ions, lanthanum ions, manganese ions, iron, chromium, copper, cobalt, nickel, fluorine, dysprosium, rhenium, europium, terbium, holmium, neodymium, or mixtures thereof.

37. The method of claim 1, wherein the composition comprises one or more radiopaque agents or contrast agents for X-ray or computed tomography (CT).

38. The method of claim 1, wherein said radiopaque or contrast agents are selected from the group consisting of barium, diatrizoate, ethiodized oil, gallium citrate, iocarmic acid, iocetamic acid, iodamide, iodipamide, iodoxamic acid, iogulamide, iohexol, iopamidol, iopanoic acid, iopromic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

39. The method of claim 1, wherein the composition comprises one or more ultrasound contrast agents.

40. The method of claim 39, wherein said ultrasound contrast agent includes a liposome or dextran.

41. The method of claim 40, wherein the liposome is gas-filled.

42. The method of claim 1, further comprising performing an operative, intravascular, laparoscopic, or endoscopic procedure.

43. The method of claim 1, further comprising administering an additional composition which comprises a therapeutic agent, a diagnostic agent, or mixtures thereof.

44. The method claim 1, wherein the composition further comprises: an immunoconjugate which comprises one or more anti-CD74 antibodies or antigen-binding fragments thereof conjugated to one or more lipids, polymeric carriers, micelles, nanoparticles, or combinations thereof; and one or more effectors.

45. The method of claim 43, wherein the composition is administered before, during, simultaneously, or after the administration of the additional composition.

46. The method of claim 43, wherein the additional composition comprises one or more drugs, prodrugs, toxins, enzymes, radioisotopes, immunomodulators, cytokines, hormones, antibodies, oligonucleotides, or combinations thereof.

47. The method of claim 46, wherein the additional composition comprises FUdR, FUdR-dO, or mixtures thereof.

48. The method of claim 43, wherein the additional composition comprises one or more hard acid chelators or soft acid chelators.

49. The method of claim 43, wherein the additional composition comprises cations selected from Group II, Group III, Group IV, Group V, transition, lanthanide or actinide metal cations, or mixtures thereof.

50. The method of claim 43, wherein the additional composition comprises cations selected from Tc, Re, Bi, Cu, As, Ag, Au, At, Pb, or mixtures thereof.

51. The method of claim 43, wherein the additional composition comprises NOTA, DOTA, DTPA, TETA, Tscg-Cys, Tsca-Cys, or mixtures thereof.

52. The method of claim 43, wherein the additional composition comprises a radionuclide.

53. The method of claim 52, wherein the radionuclide comprises 18F, 32P, 33P, 45Ti, 47Sc, 52Fe, 59Fe, 62Cu, 64Cu, 67Cu, 67Ga, 68Ga, 75Se, 77As, 86Y, 89Sr, 89Zr, 90Y, 94Tc, 94mTc, 99Mo, 99mTc, 105Pd, 105Rh, 111Ag, 111In, 123I, 124I, 125I, 131I, 142Pr, 143Pr, 149Pm, 153Sm, 154-158Gd, 161Tb, 166Dy, 166Ho, 169Er, 175Lu, 177Lu, 186Re, 188Re, 189Re, 194Ir, 198Au, 199Au, 211At, 211Pb 212Bi, 212Pb, 213Bi, 223Ra, 225Ac, or mixtures thereof.

54. The method of claim 43, wherein the additional composition comprises an enzyme.

55. The method of claim 43, wherein the enzyme comprises carboxylesterases, glucoronidases, carboxypeptidases, beta-lactamases, phosphatases, or mixtures thereof.

56. The method of claim 43, wherein the additional composition comprises an immunomodulator.

57. The method of claim 56, wherein the immunomodulator comprises IL-1, IL-2, IL-3, IL-6, IL-10, IL-12, IL-18, IL-21, interferon-α, interferon-β, interferon-γ, G-CSF, GM-CSF, or mixtures thereof.

58. The method of claim 43, wherein the additional composition comprises one or more diagnostic agents.

59. The method of claim 43, wherein the additional composition comprises one or more agents for photodynamic therapy.

60. The method of claim 59, wherein the agent for photodynamic therapy is a photosensitizer.

61. The method of claim 60, wherein the photosensitizer comprises a benzoporphyrin monoacid ring A (BDP-MA), tin etiopurpurin (SnET2), sulfonated aluminum phthalocyanine (AISPc) or lutetium texaphyrin (Lutex).

62. The method of claim 43, wherein the additional composition comprises a diagnostic radionuclide.

63. The method of claim 62, wherein the diagnostic radionuclide comprises 18F, 52Fe, 62Cu, 64Cu, 67Cu, 67Ga, 68Ga, 86Y, 89Zr, 94Tc, 94mTc 99mTc, 111In, 123I, 124I, 125I, 131I, or mixtures thereof.

64. The method of claim 62, wherein the diagnostic radionuclide emits 25-4000 keV gamma particles and/or positrons.

65. The method of claim 58, wherein the diagnostic agent is used for performing positron emission tomography (PET).

66. The method of claim 43, further comprising performing positron-emission tomography (PET).

67. The method of claim 58, wherein the diagnostic agent comprises one or more image enhancing agents and the method further comprises performing magnetic resonance imaging (MRI).

68. The method of claim 67, wherein the image enhancing agent comprises gadolinium ions, lanthanum ions, manganese ions, iron, chromium, copper, cobalt, nickel, fluorine, dysprosium, rhenium, europium, terbium, holmium, neodymium, or mixtures thereof.

69. The method of claim 43, wherein the additional composition comprises one or more radiopaque agents or contrast agents for X-ray or computed tomography (CT).

70. The method of claim 43, wherein said radiopaque or contrast agents include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

71. The method of claim 43, wherein the additional composition comprises one or more ultrasound contrast agents.

72. The method of claim 71, wherein said ultrasound contrast agent includes a liposome or dextran.

73. The method of claim 72, wherein the liposome is gas-filled.

74. The method of claim 43, further comprising performing an operative, intravascular, laparoscopic, or endoscopic procedure.

75. A method of preparing a composition comprising:
mixing one or more amphiphilic lipids with an effector to form a carrier; and contacting the carrier with a chimeric, human or humanized anti-CD74 antibody or antigen-binding fragment thereof;
wherein the anti-CD74 antibody or antigen-binding fragment thereof is an anti-CD74 diabody, a triabody, a tetrabody or an scFv and wherein the diabody, triabody, tetrabody or scFv binds to the carrier.

76. The method of claim 75, wherein one or more of the lipids comprise a maleimide group.

77. The method of claim 75, further comprising reducing the antibody.

78. The method of claim 76, further comprising reacting one or more of the maleimide groups with a free thiol group on the anti-CD74 antibody.

79. The method of claim 75, wherein the effector comprises one or more drugs, prodrugs, toxins, enzymes, radioisotopes, immunomodulators, cytokines, hormones, antibodies, oligonucleotides, or mixtures thereof.

80. The method of claim 75, further comprising mixing the carrier with one or more therapeutic or diagnostic agents.

81. A composition comprising:
one or more anti-CD74 antibodies or antigen-binding fragments thereof reactive with the epitope of CD74 to which the LL1 antibody binds;
wherein the anti-CD74 antibodies or antigen-binding fragments thereof are covalently bound to the PEG component of a PEG-lipid conjugate incorporated into a liposome;
wherein one or more effectors are incorporated into the liposome in unmodified active form, or covalently bound to the lipid component of the liposome, or covalently bound to the PEG component of the liposome;
wherein said anti-CD74 antibodies are chimeric, human or humanized; and
wherein the anti-CD74 antibody or antigen-binding fragment thereof is an anti-CD74 diabody, a triabody, a tetrabody or an scFv.

82. The composition of claim 81, wherein the one or more anti-CD74 antibodies or antigen-binding fragments thereof are conjugated to the liposome by one or more of a sulfide linkage, a hydrazone linkage, a hydrazine linkage, an ester linkage, an amido linkage, an amino linkage, an imino linkage, a thiosemicarbazone linkage, a semicarbazone linkage, an oxime linkage, a carbon-carbon linkage, or combinations thereof.

83. The composition of claim 82, wherein the anti-CD74 antibodies or antigen-binding fragments thereof are conjugated to the liposome by a sulfide linkage.

84. The composition of claim 81, further comprising one or more additional antibodies or antigen-binding fragments which specifically bind to one or more antigens selected from the group consisting of CD14, CD15, CD19, CD20, CD21, CD22, CD23, CD25, CD30, CD33, CD37, CD38, CD40, CD46, CD52, CD54, CD80, CD126, B7, Ia, HM1.24, IL-6 and combinations thereof.

85. The composition of claim 84, wherein the additional antibodies or antigen-binding fragments thereof are covalently bound to the PEG component of a PEG-lipid conjugate incorporated into a liposome.

86. The composition of claim 81, wherein the lipid component of the PEG-lipid conjugate is amphiphilic.

87. The composition of claim 81, wherein the lipid component of the PEG-lipid conjugate comprises one or more nucleophilic carbons at a distal terminus.

88. The composition of claim 81, wherein the lipid component of the PEG-lipid conjugate comprises one or more maleimide groups at a distal terminus.

89. The composition of claim 88, wherein the lipid component of the PEG-lipid conjugate comprises maleimide.

90. The composition of claim 88, wherein one or more of the anti-CD74 antibodies or antigen-binding fragments thereof are linked to one or more of the maleimide groups.

91. The composition of claim 88, wherein one or more of the anti-CD74 antibodies or antigen-binding fragments thereof are linked by one or more free thiol groups to one or more of the maleimide groups.

92. The composition of claim 81, wherein the effector comprises a therapeutic agent or a diagnostic agent.

93. The composition of claim 81, wherein the effector comprises a drug, a prodrug, a toxin, an enzyme, a radioisotope, an immunomodulator, a cytokine, an antibody or antigen-binding fragment thereof, an oligonucleotide, a photodynamic agent, or mixtures thereof.

94. The composition of claim 93, wherein the effector comprises FUdR, FUdR-dO, or mixtures thereof.

95. The composition of claim 81, further comprising one or more hard acid chelators or soft acid chelators.

96. The composition of claim 81, further comprising cations selected from Group II, Group III, Group IV, Group V, transition, lanthanide or actinide metal cations, or mixtures thereof.

97. The composition of claim 81, further comprising cations selected from Tc, Re, Bi, Cu, As, Ag, Au, At, Pb, or mixtures thereof.

98. The composition of claim 81, further comprising NOTA, DOTA, DTPA, TETA, Tscg-Cys, Tsca-Cys, or mixtures thereof.

99. The composition of claim 81, wherein the effector comprises a radionuclide.

100. The composition of claim 99, wherein the radionuclide comprises 18F, 32P, 33P, 45Ti, 47Sc, 52Fe, 59Fe, 62Cu, 64Cu, 67Cu, 67Ga, 68Ga, 75Se, 77As, 86Y, 89Sr, 89Zr, 90Y, 94Tc, 94mTc, 99Mo, 99mTc, 105Pd, 105Rh, 111Ag, 111In, 123I, 124I, 125I, 131I, 142Pr, 143Pr, 149Pm, 153Sm, 154-158Gd, 161Tb, 166Dy, 166Ho, 169Er, 175Lu, 177Lu, 186Re, 188Re, 189Re, 194Ir, 198Au, 199Au, 211At, 211Pb 212Bi, 212Pb, 213Bi, 223Ra, 225Ac, or mixtures thereof.

101. The composition of claim 81, wherein the effector comprises an enzyme.

102. The composition of claim 101, wherein the enzyme is selected from the group consisting of a carboxylesterase, a glucoronidase, a carboxypeptidase, a beta-lactamase, a phosphatase, and mixtures thereof.

103. The composition of claim 81, wherein the effector comprises an immunomodulator.

104. The composition of claim 103, wherein the immunomodulator is selected from the group consisting of IL-1, IL-2, IL-3, IL-6, IL-10, IL-12, IL-18, IL-21, interferon-α, interferon-β, interferon-γ, G-CSF, GM-C SF, and mixtures thereof.

105. The composition of claim 81, wherein the effector comprises an anti-angiogenic agent selected from the group consisting of angiostatin, endostatin, basculostatin, canstatin, maspin, an anti-VEGF binding molecule, an anti-placental growth factor binding molecule, an anti-vascular growth factor binding molecule, and mixtures thereof.

106. The composition of claim 81, wherein the anti-CD74 antibody or antigen-binding fragment thereof is conjugated to one or more therapeutic agents, diagnostic agents, or mixtures thereof.

107. The composition of claim 81, wherein the anti-CD74 antibody or antigen-binding fragment thereof comprises a fusion protein.

108. The composition of claim 107, wherein the fusion protein is multivalent.

109. A kit comprising the composition of claim 81.

* * * * *

SEQUENCE LISTING

```
<160> NUMBER OF SEQ ID NOS: 21

<210> SEQ ID NO 1
<211> LENGTH: 360
<212> TYPE: DNA
<213> ORGANISM: Mus musculus
<220> FEATURE:
<221> NAME/KEY: CDS
<222> LOCATION: (1)..(360)

<400> SEQUENCE: 1 cag atc cag ttg gtg cag tct gga cct gag ctg aag aag cct gga gag        48
Gln Ile Gln Leu Val Gln Ser Gly Pro Glu Leu Lys Lys Pro Gly Glu
  1               5                  10                  15 aca gtc aag gtc acc tgc aag act tct gga tat acc ttc aca aac tat        96
Thr Val Lys Val Thr Cys Lys Thr Ser Gly Tyr Thr Phe Thr Asn Tyr
             20                  25                  30 gga gtg aac tgg ata aag cag act cca gga gag ggt tta cag tgg atg       144
Gly Val Asn Trp Ile Lys Gln Thr Pro Gly Glu Gly Leu Gln Trp Met
         35                  40                  45 ggc tgg ata aac ccc aac act gga gag cca aca ttt gat gat gac ttc       192
Gly Trp Ile Asn Pro Asn Thr Gly Glu Pro Thr Phe Asp Asp Asp Phe
     50                  55                  60 aag gga cga ttt gcc ttc tct ttg gaa tcc tct gcc agc act gcc ttt       240
Lys Gly Arg Phe Ala Phe Ser Leu Glu Ser Ser Ala Ser Thr Ala Phe
 65                  70                  75                  80 ttg cag atc agc aac ctc aaa aat gag gac atg ggt aca tat ttc tgt       288
Leu Gln Ile Ser Asn Leu Lys Asn Glu Asp Met Gly Thr Tyr Phe Cys
                 85                  90                  95 tca aga tcg agg ggt aaa aac gaa gcc tgg ttt gct tat tgg ggc caa       336
Ser Arg Ser Arg Gly Lys Asn Glu Ala Trp Phe Ala Tyr Trp Gly Gln
            100                 105                 110 ggg act ctg gtc act gtc tct gaa                                       360
Gly Thr Leu Val Thr Val Ser Glu
```

<210> SEQ ID NO 2
<211> LENGTH: 120
<212> TYPE: PRT
<213> ORGANISM: Mus musculus

<400> SEQUENCE: 2

Gln Ile Gln Leu Val Gln Ser Gly Pro Glu Leu Lys Lys Pro Gly Glu
 1               5                  10                  15

Thr Val Lys Val Thr Cys Lys Thr Ser Gly Tyr Thr Phe Thr Asn Tyr
            20                  25                  30

Gly Val Asn Trp Ile Lys Gln Thr Pro Gly Glu Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Glu Ser Ser Ala Ser Thr Ala Phe
65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Glu
        115                 120

<210> SEQ ID NO 3
<211> LENGTH: 337
<212> TYPE: DNA
<213> ORGANISM: Mus musculus
<220> FEATURE:
<221> NAME/KEY: CDS
<222> LOCATION: (1)..(333)

<400> SEQUENCE: 3 gat gtt gtg atg acc caa act cca ctc tcc ctg cct gtc agt ctt gga     48
Asp Val Val Met Thr Gln Thr Pro Leu Ser Leu Pro Val Ser Leu Gly
 1               5                  10                  15 gat caa gcc tcc atc tct tgc aga tct agt cag agc ctt gta cac aga     96
Asp Gln Ala Ser Ile Ser Cys Arg Ser Ser Gln Ser Leu Val His Arg
            20                  25                  30 aat gga aac acc tat tta cat tgg tac ctg cag aag cca ggc cag tct    144
Asn Gly Asn Thr Tyr Leu His Trp Tyr Leu Gln Lys Pro Gly Gln Ser
        35                  40                  45 cca aag ctc ctg atc tac aca gtt tcc aac cga ttt tct ggg gtc cca    192
Pro Lys Leu Leu Ile Tyr Thr Val Ser Asn Arg Phe Ser Gly Val Pro
    50                  55                  60 gac agg ttc agt ggc agt gga tca ggg aca gat ttc aca ctc aag atc    240
Asp Arg Phe Ser Gly Ser Gly Ser Gly Thr Asp Phe Thr Leu Lys Ile
65                  70                  75                  80 agt aga gtg gag gct gag gat ctg gga ctt tat ttc tgc tct caa agt    288
Ser Arg Val Glu Ala Glu Asp Leu Gly Leu Tyr Phe Cys Ser Gln Ser
                85                  90                  95 tca cat gtt cct ccc acg ttc ggt gct ggg acc aag ctg gag atc taac   337
Ser His Val Pro Pro Thr Phe Gly Ala Gly Thr Lys Leu Glu Ile
            100                 105                 110

<210> SEQ ID NO 4
<211> LENGTH: 111
<212> TYPE: PRT
<213> ORGANISM: Mus musculus -continued

<400> SEQUENCE: 4

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Arg
             20                  25                  30

Asn Gly Asn Thr Tyr Leu His Trp Tyr Leu Gln Lys Pro Gly Gln Ser
         35                  40                  45

Pro Lys Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Phe Cys Ser Gln Ser
                 85                  90                  95

Ser His Val Pro Pro Thr Phe Gly Ala Gly Thr Lys Leu Glu Ile
            100                 105                 110
```

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: chimeric
      cLL1VH sequence
<220> FEATURE:
<221> NAME/KEY: CDS
<222> LOCATION: (1)..(360)

<400> SEQUENCE: 5

```
cag gtc caa ctg cag cag tct gga cct gag ctg aag aag cct gga gag     48
Gln Val Gln Leu Gln Gln Ser Gly Pro Glu Leu Lys Lys Pro Gly Glu
  1               5                  10                  15 aca gtc aag gtc acc tgc aag act tct gga tat acc ttc aca aac tat     96
Thr Val Lys Val Thr Cys Lys Thr Ser Gly Tyr Thr Phe Thr Asn Tyr
             20                  25                  30 gga gtg aac tgg ata aag cag act cca gga gag ggt tta cag tgg atg    144
Gly Val Asn Trp Ile Lys Gln Thr Pro Gly Glu Gly Leu Gln Trp Met
         35                  40                  45 ggc tgg ata aac ccc aac act gga gag cca aca ttt gat gat gac ttc    192
Gly Trp Ile Asn Pro Asn Thr Gly Glu Pro Thr Phe Asp Asp Asp Phe
     50                  55                  60 aag gga cga ttt gcc ttc tct ttg gaa tcc tct gcc agc act gcc ttt    240
Lys Gly Arg Phe Ala Phe Ser Leu Glu Ser Ser Ala Ser Thr Ala Phe
 65                  70                  75                  80 ttg cag atc agc aac ctc aaa aat gag gac atg ggt aca tat ttc tgt    288
Leu Gln Ile Ser Asn Leu Lys Asn Glu Asp Met Gly Thr Tyr Phe Cys
                 85                  90                  95 tca aga tcg agg ggt aaa aac gaa gcc tgg ttt gct tat tgg ggc caa    336
Ser Arg Ser Arg Gly Lys Asn Glu Ala Trp Phe Ala Tyr Trp Gly Gln
            100                 105                 110 ggg act ctg gtc acc gtc tcc tca                                    360
Gly Thr Leu Val Thr Val Ser Ser
            115                 120
```

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: chimeric
      cLL1VH sequence

<400> SEQUENCE: 6

```
Gln Val Gln Leu Gln Gln Ser Gly Pro Glu Leu Lys Lys Pro Gly Glu
 1               5                  10                  15

Thr Val Lys Val Thr Cys Lys Thr Ser Gly Tyr Thr Phe Thr Asn Tyr
            20                  25                  30

Gly Val Asn Trp Ile Lys Gln Thr Pro Gly Glu Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Glu Ser Ala Ser Thr Ala Phe
 65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120
```

<210> SEQ ID NO 7
<211> LENGTH: 339
<212> TYPE: DNA
<213> ORGANISM: Artificial Sequence
<220> FEATURE:
<223> OTHER INFORMATION: Description of Artificial Sequence: chimeric cLL1Vk sequence
<220> FEATURE:
<221> NAME/KEY: CDS
<222> LOCATION: (1)..(339)

<400> SEQUENCE: 7

```
gac atc cag ctg acc caa act cca ctc tcc ctg cct gtc agt ctt gga    48
Asp Ile Gln Leu Thr Gln Thr Pro Leu Ser Leu Pro Val Ser Leu Gly
 1               5                  10                  15 gat caa gcc tcc atc tct tgc aga tct agt cag agc ctt gta cac aga    96
Asp Gln Ala Ser Ile Ser Cys Arg Ser Ser Gln Ser Leu Val His Arg
            20                  25                  30 aat gga aac acc tat tta cat tgg tac ctg cag aag cca ggc cag tct   144
Asn Gly Asn Thr Tyr Leu His Trp Tyr Leu Gln Lys Pro Gly Gln Ser
        35                  40                  45 cca aag ctc ctg atc tac aca gtt tcc aac cga ttt tct ggg gtc cca   192
Pro Lys Leu Leu Ile Tyr Thr Val Ser Asn Arg Phe Ser Gly Val Pro
    50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
 65                  70                  75                  80 agt aga gtg gag gct gag gat ctg gga ctt tat ttc tgc tct caa agt   288
Ser Arg Val Glu Ala Glu Asp Leu Gly Leu Tyr Phe Cys Ser Gln Ser
                85                  90                  95 tca cat gtt cct ccc acg ttc ggt gct ggg acc aag ctg gag atc aaa   336
Ser His Val Pro Pro Thr Phe Gly Ala Gly Thr Lys Leu Glu Ile Lys
            100                 105                 110 cgt                                                               339
Arg
```

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: chimeric cLL1Vk sequence

<400> SEQUENCE: 8

```
Asp Ile Gln Leu Thr Gln Thr Pro Leu Ser Leu Pro Val Ser Leu Gly
  1               5                  10                  15

Asp Gln Ala Ser Ile Ser Cys Arg Ser Ser Gln Ser Leu Val His Arg
             20                  25                  30

Asn Gly Asn Thr Tyr Leu His Trp Tyr Leu Gln Lys Pro Gly Gln Ser
         35                  40                  45

Pro Lys Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Phe Cys Ser Gln Ser
                 85                  90                  95

Ser His Val Pro Pro Thr Phe Gly Ala Gly Thr Lys Leu Glu Ile Lys
            100                 105                 110

Arg
```

<210> SEQ ID NO 9
<211> LENGTH: 360
<212> TYPE: DNA
<213> ORGANISM: Artificial Sequence
<220> FEATURE:
<223> OTHER INFORMATION: Description of Artificial Sequence: humanized hLL1VH sequence
<220> FEATURE:
<221> NAME/KEY: CDS
<222> LOCATION: (1)..(360)

<400> SEQUENCE: 9

```
cag gtc caa ctg cag caa tct ggg tct gag ttg aag aag cct ggg gcc      48
Gln Val Gln Leu Gln Gln Ser Gly Ser Glu Leu Lys Lys Pro Gly Ala
  1               5                  10                  15 tca gtg aag gtt tcc tgc aag gct tct gga tac acc ttc act aac tat      96
Ser Val Lys Val Ser Cys Lys Ala Ser Gly Tyr Thr Phe Thr Asn Tyr
             20                  25                  30 gga gtg aac tgg ata aag cag gcc cct gga caa ggg ctt cag tgg atg     144
Gly Val Asn Trp Ile Lys Gln Ala Pro Gly Gln Gly Leu Gln Trp Met
         35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
     50                  55                  60 aag gga cga ttt gcc ttc tcc ttg gac acc tct gtc agc acg gca tat     240
Lys Gly Arg Phe Ala Phe Ser Leu Asp Thr Ser Val Ser Thr Ala Tyr
 65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                 85                  90                  95 tca aga tcg agg ggt aaa aac gaa gcc tgg ttt gct tat tgg ggc caa     336
Ser Arg Ser Arg Gly Lys Asn Glu Ala Trp Phe Ala Tyr Trp Gly Gln
            100                 105                 110 ggg acc ctg gtc acc gtc tcc tca                                     360
Gly Thr Leu Val Thr Val Ser Ser
        115                 120
```

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: humanized hLL1VH sequence -continued

<400> SEQUENCE: 10

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Ile Lys Gln Ala Pro Gly Gln Gly Leu Gln Trp Met
        35                  40                  45

Gly Trp Ile Asn Pro Asn Thr Gly Glu Pro Thr Phe Asp Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
            100                 105                 110

Gly Thr Leu Val Thr Val Ser Ser
        115                 120

<210> SEQ ID NO 11
<211> LENGTH: 339
<212> TYPE: DNA
<213> ORGANISM: Artificial Sequence
<220> FEATURE:
<223> OTHER INFORMATION: Description of Artificial Sequence: humanized
      hLL1Vk sequence
<220> FEATURE:
<221> NAME/KEY: CDS
<222> LOCATION: (1)..(339)

<400> SEQUENCE: 11 gac atc cag ctg act cag tct cca ctc tcc ctg ccc gtc acc ctt gga       48
Asp Ile Gln Leu Thr Gln Ser Pro Leu Ser Leu Pro Val Thr Leu Gly
1               5                   10                  15 cag ccg gcc tcc atc tcc tgc aga tca agt cag agc ctt gta cac aga       96
Gln Pro Ala Ser Ile Ser Cys Arg Ser Ser Gln Ser Leu Val His Arg
            20                  25                  30 aat gga aac acc tat tta cat tgg ttt cag cag agg cca ggc caa tct      144
Asn Gly Asn Thr Tyr Leu His Trp Phe Gln Gln Arg Pro Gly Gln Ser
        35                  40                  45 cca agg ctc ctg atc tac aca gtt tcc aac cga ttt tct ggg gtc cca      192
Pro Arg Leu Leu Ile Tyr Thr Val Ser Asn Arg Phe Ser Gly Val Pro
    50                  55                  60 gac aga ttc agc ggc agt ggg tca ggc act gat ttc aca ctg aaa atc      240
Asp Arg Phe Ser Gly Ser Gly Ser Gly Thr Asp Phe Thr Leu Lys Ile
65                  70                  75                  80 agc agg gtg gag gct gag gat gtt ggg gtt tat ttc tgc tct caa agt      288
Ser Arg Val Glu Ala Glu Asp Val Gly Val Tyr Phe Cys Ser Gln Ser
                85                  90                  95 tca cat gtt cct ccc acg ttc ggt gct ggg aca cga ctg gag atc aaa      336
Ser His Val Pro Pro Thr Phe Gly Ala Gly Thr Arg Leu Glu Ile Lys
            100                 105                 110 cgt                                                                   339
Arg

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: humanized hLL1Vk sequence

<400> SEQUENCE: 12

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110

Arg

<210> SEQ ID NO 13
<211> LENGTH: 109
<212> TYPE: PRT
<213> ORGANISM: Homo sapiens

<400> SEQUENCE: 13

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Glu Asp Ser Asn Gly Tyr Lys Ile Phe Asp Tyr
            100                 105

<210> SEQ ID NO 14
<211> LENGTH: 11
<212> TYPE: PRT
<213> ORGANISM: Homo sapiens

<400> SEQUENCE: 14

Trp Gly Gln Gly Ser Leu Val Thr Val Ser Ser
1               5                   10

<210> SEQ ID NO 15
<211> LENGTH: 111
<212> TYPE: PRT
<213> ORGANISM: Homo sapiens

<400> SEQUENCE: 15

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser

-continued

```
                  20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Phe Thr Phe Gly Gln Gly Thr Arg Leu Glu Ile
            100                 105                 110
```

<210> SEQ ID NO 16
<211> LENGTH: 16
<212> TYPE: PRT
<213> ORGANISM: Mus musculus

<400> SEQUENCE: 16

```
Arg Ser Ser Gln Ser Leu Val His Arg Asn Gly Asn Thr Tyr Leu His
 1               5                  10                  15
```

<210> SEQ ID NO 17
<211> LENGTH: 7
<212> TYPE: PRT
<213> ORGANISM: Mus musculus

<400> SEQUENCE: 17

```
Thr Val Ser Asn Arg Phe Ser
 1               5
```

<210> SEQ ID NO 18
<211> LENGTH: 9
<212> TYPE: PRT
<213> ORGANISM: Mus musculus

<400> SEQUENCE: 18

```
Ser Gln Ser Ser His Val Pro Pro Thr
 1               5
```

<210> SEQ ID NO 19
<211> LENGTH: 5
<212> TYPE: PRT
<213> ORGANISM: Mus musculus

<400> SEQUENCE: 19

```
Asn Tyr Gly Val Asn
 1               5
```

<210> SEQ ID NO 20
<211> LENGTH: 17
<212> TYPE: PRT
<213> ORGANISM: Mus musculus

<400> SEQUENCE: 20

```
Trp Ile Asn Pro Asn Thr Gly Glu Pro Thr Phe Asp Asp Asp Phe Lys
 1               5                  10                  15

Gly
```

```
<210> SEQ ID NO 21
<211> LENGTH: 11
<212> TYPE: PRT
<213> ORGANISM: Mus musculus

<400> SEQUENCE: 21

Ser Arg Gly Lys Asn Glu Ala Trp Phe Ala Tyr
1               5                   10
```